US008853151B2

(12) United States Patent
Baker, Jr. et al.

(10) Patent No.: US 8,853,151 B2
(45) Date of Patent: Oct. 7, 2014

(54) PRO-DRUG COMPLEXES AND RELATED METHODS OF USE

(75) Inventors: James R. Baker, Jr., Ann Arbor, MI (US); Baohua M. Huang, Ann Arbor, MI (US); Thommey P. Thomas, Dexter, MI (US)

(73) Assignee: The Regents of the University of Michigan, Ann Harbor, MI (US)

( * ) Notice: Subject to any disclaimer, the term of this patent is extended or adjusted under 35 U.S.C. 154(b) by 72 days.

(21) Appl. No.: 13/378,178

(22) PCT Filed: Jun. 30, 2010

(86) PCT No.: PCT/US2010/040546
§ 371 (c)(1),
(2), (4) Date: Mar. 12, 2012

(87) PCT Pub. No.: WO2011/002852
PCT Pub. Date: Jan. 6, 2011

(65) Prior Publication Data
US 2012/0171227 A1    Jul. 5, 2012

Related U.S. Application Data

(60) Provisional application No. 61/221,596, filed on Jun. 30, 2009.

(51) Int. Cl.
| | |
|---|---|
| *A61K 31/4745* | (2006.01) |
| *A61K 38/12* | (2006.01) |
| *C07D 491/147* | (2006.01) |
| *C07K 7/64* | (2006.01) |
| *A61K 31/437* | (2006.01) |
| *A61K 47/48* | (2006.01) |

(52) U.S. Cl.
CPC ......... *A61K 31/437* (2013.01); *A61K 47/48246* (2013.01)
USPC ........... 514/1.3; 514/19.9; 514/283; 530/321; 546/48

(58) Field of Classification Search
None
See application file for complete search history.

(56) References Cited

U.S. PATENT DOCUMENTS

| | | | |
|---|---|---|---|
| 4,473,692 | A | 9/1984 | Miyasaka |
| 2006/0193865 | A1 | 8/2006 | Govindan |
| 2008/0033003 | A1* | 2/2008 | Pisano et al. .................. 514/283 |
| 2008/0166363 | A1* | 7/2008 | Govindan et al. .......... 424/178.1 |
| 2008/0267882 | A1 | 10/2008 | Chen |
| 2008/0292556 | A1* | 11/2008 | Texier-Nogues et al. ...... 424/9.6 |

OTHER PUBLICATIONS

Burke et al. Design, Synthesis, and Biological Evaluation of Antibody-Drug Conjugates Comprised of Potent Camptothecin Analogues. Bioconjugate Chemistry. May 26, 2009, vol. 20, No. 6, pp. 1242-1250.*

(Continued)

*Primary Examiner* — Jeffrey E Russel
(74) *Attorney, Agent, or Firm* — Casimir Jones SC

(57) ABSTRACT

The present invention provides methods, compositions and applications for efficient, site-specific drug delivery using pro-drug complexes comprising one or more functional groups (e.g., imaging agents, targeting agents, and trigger agents) conjugated with a therapeutic agent (e.g., a chemotherapeutic agent), methods of synthesizing the same, as well as systems and methods utilizing the therapeutic and diagnostic compositions (e.g., in diagnostic and/or therapeutic settings (e.g., for the delivery of therapeutics, imaging, and/or targeting agents (e.g., in disease (e.g., cancer) diagnosis and/or therapy, etc.))). Trigger agents include an indolequinone; attachment groups include a triazole ring; and therapeutic agents include camptothecin.

2 Claims, 9 Drawing Sheets

(56) References Cited

OTHER PUBLICATIONS

Huang et al. The Synthesis of a c(RGDyK) Targeted SN38 Prodrug with an Indolequinone Structure for Bioreductive Drug Release. Organic Letters. Mar. 1, 2010, vol. 12, No. 7, pp. 1384-1387.*
Huang, B., et al., "Copper-free click conjugation of methotrexate to a PAMAM dendrimer platform", Tetrahedron Letters, E-pub, Dec. 10, 2010, v. 52, pp. 1411-1414.
Dijk, M.V., et al., "Synthesis and Applications of Biomedical and Pharmaceutical Polymers via Click Chemistry Methodologies," Bioconjugate Chemistry, Nov. 2009, v. 20, No. 11, pp. 2011-2016.
Nimmo, C.M. et al., "Regenerative Biomaterials that 'Click': Simple, Aqueous-Based Protocols for Hydrogel Synthesis, Surface Immoboilization, and 3D Patterning" Bioconjugate Chemistry, Oct. 13, 2011, v. 22, pp. 2199-2209.
Huang, B., et al., "The facile synthesis of multifunctional PAMAM dendrimer conjugates through copper-free click chemistry" Bioorganic & Medicinal Chemistry Letters, Mar. 21, 2012, v. 22, pp. 3152-3156.
International Search Report and Written Opinion mailed Mar. 29, 2013, International Patent Application No. PCT/US2012/066104.
Araki, E., et al., Relationship between development of diarrhea and the concentration of SN-38, an active metabolite of CPT-11, in the intestine and the blood plasma of athymic mice following intraperitoneal administration of CPT-11. Jpn. J. Cancer Res. 84 697-702 (Jun. 1993).
Atsumi, R., et al., Identification of the metabolites of irinotecan, a new derivative of camptothecin, in rat bile and its bilary excretion, Xenobiotica, 21: 1159-1169 (1991).
Barilero, L., et al., Simultaneous determination of the camptothecin analogue (PT-11 and its active metabolite SN-38 by high-performance liquid chromatography; application to plasma pharmacokinetic studies in cancer patients. J. Chromatogr. 575:275-280 (1992).
Emerson, D. L., "Liposomal delivery of camptothecins," Pharm. Sci. and Tech. Today, 3, 205-209 (2000).
Gupta et al., "Metabolic fate of irinotecan in humans: correlation of glucuronidation with diarrhea," Cancer Res. 54, 3723-3725 (Jul. 15, 1994).
Innocenti et al., "Pharmacogenetics of anticancer agents: Lessons from amonafide and irinotecan," Drug Metabolism and Disposition, vol. 29, No. 4, Part 2, 596-600 (2001).
International Search Report mailed Mar. 29, 2011, International Patent Application No. PCT/US2010/040546.
Iyer et al. "Phenotype-genotype correlation of in vitro SN-38 (active metabolite of irinotecan) and bilirubin glucuronidation in human liver tissue with UGTI A1 promoter polymorphism," Clin. Pharmacol. Ther., 65, 576-582 (1999).
Iyer et al., "Genetic predisposition to the metabolism of irinotecan (CPT-11). Role of uridine diphosphate glucuronosyltransferase isoform 1A1 in the glucuronidation of its active metabolite (SN-38) in human liver microsomes," J Clin Invest 101:847-854, (1998).
Iyer et al., "UGTIA1 *28 polymorphism as a determinant of irinotecan disposition and toxicity," Pharmacogenetics, 2, 43-47 (2002).
Kaneda, N., et al. Metabolism and pharmacokinetics of the camptothecin analogue CPT-11 in the mouse. Cancer Res. 50:1715-1720 (Mar. 15, 1990).
Kawato, Y., et al., Intracellular roles of SN-38, a metabolite of the camptothecin derivative CPT-11, in the anti-tumor effect of CPT-11, Cancer Res. 51:4187-4191 (Aug. 15, 1991).
Kehrer et al., "Factors involved in prolongation of the terminal disposition phase of SN-38: clinical and experimental studies," Clin. Cancer Res., 6, 3451-3458 (2000).

Lavelle et al. "Preclinical evaluation of CPT-11 and its active metabolite SN-38," Semin. Oncol., 23, 11-20 (1996).
Mathijssen et al., "Impact of body-size measures on irinotecan clearance: alternative dosing recommendations," J. Clin. Oncol., 20, 81-87 (2002).
Matsuzaki, T., et al., Inhibition of spontaneous and experimental metastasis by a new derivative of camptothecin, CPT-11, in mice, Cancer Chemother. Pharmacol. 21: 308-312 (1988).
Negoro, S., et al., Phase I study of weekly intravenous infusion of CPT-11, a new derivative of camptothecin, in the treatment of advanced non-small-cell lung cancer. J. Natl. Cancer Inst. 83: 1164-1168 (1991).
Ohe, Y., et al., Phase I study and pharmacokinietics of CPT-11 with 5-day continuous infusion. J. Natl. Cancer Inst. 84: 972-974 (1992).
O'Leary et al., "Antiangiogenic Effects of Camptothecin Analogues 9-Amino-20(S)-camptothecin, Topotecan, and CPT-11 Studied in the Mouse Cornea Model," Clinical Cancer Research, 5, 181-187 (1999).
Peikov, V., et al, ph-Dependent Association of SN-38 with Lipid Bilayers of a Novel Liposomal Formulation, International Journal of Pharmaceutics 299 (2005) 92-99.
Pitot et al, "Phase I dose-finding and pharmacokinetic trial of irinotecan hydrochloride (CPT-11) using a once-every-three-week dosing schedule for patients with advanced solid tumor malignancy," Clin Cancer Res., 6, 2236-2244 (2000).
Pizzolato et al., "The camptothecins," The Lancet, 361, 2235-2242 (2003).
Rivory et al, "Kinetics of the in vivo interconversion of the carboxylate and lactone forms of irinotecan (CPT-11) and of its metabolite SN-38 in patients," Cancer Res. 54:6330-6333, (1994).
Rivory et al, "Pharmacokinetic interrelationships of irinotecan (CPT-11) and its-three major plasma metabolites in patients enrolled in phase I/II trials," Clin. Cancer Res., 3, 1261-1266 (1997).
Rivory, "Metabolism of CPT-11 impact on activity," Ann. N.Y. Acad. Sci., 922, 205-215 (2000).
Rothenberg, M., et al., Phase I and pharmacokinetic trial of weekly CPT-11. J. Clin. Oncol. 11:2194-2204 (1993).
Rowinsky, E.K., et al., Phase I and pharmacological study of the novel topoisomerase I inhibitor 7-ethyl-10-[4-(1-piperidino)-I-piperidino)carbonyloxycamptothecin (CPT-11) administered as a ninety-minute infusion every 3 weeks. Cancer Res. 54: 427-436 (1994).
Sadzuka et al., "Effect of liposomalization on the antitumor activity, side-effects and tissue distribution of CPT-11," Cancer Letters, 127, 99-106 (1998).
Sanghani et al., "Carboxylesterases expressed in human colon tumor tissue and their role in CPT-11 hydrolysis," Clin. Cancer Res., 9(13), 4983-4991 (Oct. 15, 2003).
Sasaki et al., "Pharmacological correlation between total drug concentration and lactones of CPT-11 and SN-38 in patients treated with CPT-11," Cancer Res., 86, 111-116 (1995).
Slatter et al., "Pharmacokinetics, metabolism and excretion of irinotecan (CPT-11) following iv infusion of [14C] CPT-11 in cancer patients," Drug Metab. Dispos., 28, 423-433 (2000).
Tsuji, T., et al., CPT-11 converting enzyme from rat serum; purification and some properties, J. Pharmacobio-Dyn., 14:341-349 (1991).
Tsuruo, T., et al., Antitumor effect of CPT-11, a new derivative of camptothecin, against pleiotropic drug-resistant tumors in vitro and in vivo, Cancer Chemother. Pharmacol. 21:71-74 (1988).
Zhang, J. Allen, t al, Development and Characterization of a Novel Liposome-Based Formulation of SN-38, International Journal of Pharmaceutics 270 (2004) 93-107.
Zhang, Z., "Bioreduction activated prodrugs of camptothecin: molecular design, synthesis, activation mechanism and hypoxia selective cytotoxicity," Org. Biomol. Chem., 2005, vol. 3, pp. 1905-1910.
Zhao, H., et al., "Novel Prodrugs of SN38 Using Multiarm Poly(ethylene glycol) Linkers," Bioconjugate Chem., 2008, vol. 19, pp. 849-859.

* cited by examiner

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The residue at this position is linked to
      (7-methoxycoumarin-4-yl)acetyl
<220> FEATURE:
<221> NAME/KEY: MISC_FEATURE
<222> LOCATION: (7)..(7)
<223> OTHER INFORMATION: The residue at this position is linked to a
      2,4-dinitrophenyl group and NH2

<400> SEQUENCE: 1

Tyr Glu Val Asp Gly Trp Lys
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

His Leu Asn Ile Leu Ser Thr Leu Trp Lys Tyr Arg
1               5                   10
```

PRO-DRUG COMPLEXES AND RELATED METHODS OF USE

CROSS-REFERENCE TO RELATED APPLICATIONS

This application is a U.S. §371 National Phase Entry of International Patent Application No. PCT/US2010/040546, International Filing Date Jun. 30, 2010, which claims the benefit of priority to U.S. Provisional Patent Application No. 61/221,596, filed Jun. 30, 2009, the contents of which are hereby incorporated by reference their entireties.

STATEMENT REGARDING FEDERALLY SPONSORED RESEARCH OR DEVELOPMENT

None.

FIELD OF THE INVENTION

The present invention provides methods, compositions and applications for efficient, site-specific drug delivery using pro-drug complexes comprising one or more functional groups (e.g., imaging agents, targeting agents, and trigger agents) conjugated with a therapeutic agent (e.g., a chemotherapeutic agent), methods of synthesizing the same, as well as systems and methods utilizing the therapeutic and diagnostic compositions (e.g., in diagnostic and/or therapeutic settings (e.g., for the delivery of therapeutics, imaging, and/or targeting agents (e.g., in disease (e.g., cancer) diagnosis and/or therapy, etc.).

BACKGROUND OF THE INVENTION

Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor but some, like leukemia, do not. The branch of medicine concerned with the study, diagnosis, treatment, and prevention of cancer is oncology.

Cancer may affect people at all ages, even fetuses, but the risk for most varieties increases with age. Cancer causes about 13% of all human deaths. According to the American Cancer Society, 7.6 million people died from cancer in the world during 2007. Cancers can affect all animals.

Nearly all cancers are caused by abnormalities in the genetic material of the transformed cells. These abnormalities may be due to the effects of carcinogens, such as tobacco smoke, radiation, chemicals, or infectious agents. Other cancer-promoting genetic abnormalities may be randomly acquired through errors in DNA replication, or are inherited, and thus present in all cells from birth. The heritability of cancers are usually affected by complex interactions between carcinogens and the host's genome. New aspects of the genetics of cancer pathogenesis, such as DNA methylation, and microRNAs are increasingly recognized as important.

Genetic abnormalities found in cancer typically affect two general classes of genes. Cancer-promoting oncogenes are typically activated in cancer cells, giving those cells new properties, such as hyperactive growth and division, protection against programmed cell death, loss of respect for normal tissue boundaries, and the ability to become established in diverse tissue environments. Tumor suppressor genes are then inactivated in cancer cells, resulting in the loss of normal functions in those cells, such as accurate DNA replication, control over the cell cycle, orientation and adhesion within tissues, and interaction with protective cells of the immune system.

Diagnosis usually requires the histologic examination of a tissue biopsy specimen by a pathologist, although the initial indication of malignancy can be symptoms or radiographic imaging abnormalities. Most cancers can be treated and some cured, depending on the specific type, location, and stage.

Once diagnosed, cancer is usually treated with a combination of surgery, chemotherapy and radiotherapy. As research develops, treatments are becoming more specific for different varieties of cancer. Many standard cancer chemotherapeutic drugs kill cancer cells upon induction of programmed cell death ("apoptosis") by targeting basic cellular processes and molecules. These basic cellular processes and molecules include RNA/DNA (alkylating and carbamylating agents, platin analogs and topoisomerase inhibitors), metabolism (drugs of this class are named anti-metabolites and examples are folic acid, purine and pyrimidine antagonist) as well as the mitotic spindle apparatus with $\alpha,\beta$-tubulin heterodimers as the essential component (drugs are categorized into stabilizing and destabilizing tubulin inhibitors; examples are Taxol/Paclitaxel®, Docetaxel/Taxotere® and vinca alkaloids). Yet agents such as these are insufficient treatments, as evidenced by the following statistics for breast, prostrate, and lung cancer, for example.

In view of the foregoing, the need exists for more effective compositions and methods for treating cancers of all types, including prostrate, breast, and lung cancers, as well as colon cancer, ovarian cancer, leukemia, renal cancer, melanoma and central nervous system cancer. The present invention addresses this need and has other related advantages.

SUMMARY

The present invention provides methods, compositions and applications for efficient, site-specific drug delivery using pro-drug complexes comprising therapeutic agents and one or more functional groups (e.g., imaging agents, targeting agents, and trigger agents). In particular, the present invention relates to pro-drug complexes comprising one or more functional groups conjugated with a therapeutic agent (e.g., a chemotherapeutic agent), methods of synthesizing the same, as well as systems and methods utilizing the therapeutic and diagnostic compositions (e.g., in diagnostic and/or therapeutic settings (e.g., for the delivery of therapeutics, imaging, and/or targeting agents (e.g., in disease (e.g., cancer) diagnosis and/or therapy, etc.).

In experiments conducted during the course of developing embodiments for the present invention, pro-drug complexes containing functional components were developed having a therapeutic agent (e.g., a chemotherapeutic agent) conjugated with one or more functional groups (e.g., a trigger agent (e.g., for release under hypoxic conditions), and a targeting agent (e.g., a targeting agent specific for $\alpha_v\beta_3$ integrin)). The present invention synthesized camptothecin (or camptothecin based derivative) pro-drug complexes having functional groups. In particular, prb-drug complexes were synthesized with the camptothecin derivative SN-38 conjugated with a trigger agent (e.g., an indolequinone structure for hypoxia triggered drug release) and a targeting agent (e.g., c(RGDyK) for targeting the $\alpha_v\beta_3$ integrin). The SN-38 pro-drug complexes demonstrated high water solubility (e.g., the SN-38 prodrug complex demonstrated solubility greater than or equal to 50 times the solubility of SN-38) (e.g., the SN-38 pro-drug complex demonstrated a solubility of 100 micro gram per milliliter of water versus about 2 micro gram per milliliter for SN38), triple tumor specificity (e.g., hypoxia, DT-Diaphorase, and $\alpha_v\beta_3$ integrin), and prolonged systemic circulation time. Moreover, the SN-38 pro-drug complexes were shown to inhibit cancer cell growth.

Accordingly, in certain embodiments, the present invention provides pro-drug complexes comprising a therapeutic agent and one or more functional groups, wherein each of the one or more functional groups is selected from a targeting agent, a trigger agent, and an imaging agent. The arrangement of the therapeutic agent and the one or more functional groups is not limited to a particular configuration. Indeed, in some embodiments, the arrangement of the therapeutic agent and the one or more functional groups is represented by one of the following formulas:

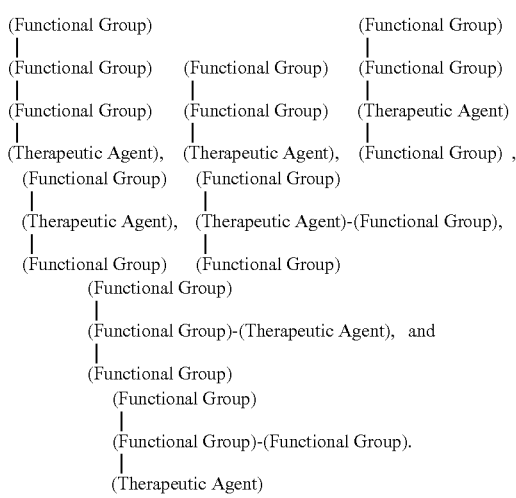

In some embodiments, the therapeutic agent is, for example, a chemotherapeutic agent, an anti-oncogenic agent, an anti-angiogenic agent, a tumor suppressor agent, an antimicrobial agent, an expression construct comprising a nucleic acid encoding a therapeutic protein, etc. In some embodiments, the therapeutic agent is a camptothecin derivative such as, for example, SN-38.

In some embodiments, the trigger agent is configured, for example, to delay release of the therapeutic agent, to constitutively release the therapeutic agent, to release the therapeutic agent under conditions of acidosis, to release the therapeutic agent under conditions of hypoxia, and to release the therapeutic agent in the presence of a brain enzyme (e.g., DT-diaphorase). In some embodiments, the trigger agent is, for example, an ester bond, an amide bond, an ether bond, an indoquinone, a nitroheterocyle, and a nitroimidazole. In some embodiments, the trigger agent is indolequinone.

In some embodiments, the imaging agent is fluorescein isothiocyanate or 6-TAMARA.

In some embodiments, the targeting agent is configured to target the pro-drug complex to cancer cells. Examples of such targeting agents include, but are not limited to, c(RGDyK), folic acid, CFTR, EGFR, estrogen receptor, FGR2, folate receptor, IL-2 receptor, and VEGFR. In some embodiments, the targeting agent is an antibody that binds to a polypeptide selected from, for example, p53, Muc1, a mutated version of p53 that is present in breast cancer, HER-2, T and Tn haptens in glycoproteins of human breast carcinoma, and MSA breast carcinoma glycoprotein. In some embodiments, the antibody is human carcinoma antigen, TP1 and TP3 antigens from osteocarcinoma cells, Thomsen-Friedenreich (TF) antigen from adenocarcinoma cells, KC-4 antigen from human prostrate adenocarcinoma, human colorectal cancer antigen, CA125 antigen from cystadenocarcinoma, DF3 antigen from human breast carcinoma, and p97 antigen of human melanoma, carcinoma or orosomucoid-related antigen.

In some embodiments, one or more of the attachments between the therapeutic agent and one or more of the functional groups (or the attachment between the functional groups) are accomplished with a linker. In some embodiments the linker has a spacer comprising between 1 and 50 straight or branched (e.g., substituted or unsubstituted) carbon chains. In some embodiments, the linker is

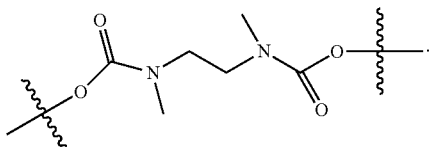 [SMILES: *OC(=O)N(C)CCN(C)C(=O)O*]

In some embodiments, one or more of the attachments between the therapeutic agent and one or more of the functional groups (or the attachment between the functional groups) are accomplished with via a 1,3 dipolar cycloaddition reaction. In some embodiments, one or more of the attachments between the therapeutic agent and one or more of the functional groups (or the attachment between the functional groups) comprises a triazole ring.

In some embodiments, the pro-drug complex is represented by the formula: R1-R2-R3, wherein R1 is SN-38, R2 is indolequinone, and R3 is c(RGDyK). In such embodiments, R1 and R2 and conjugated via a linker represented by

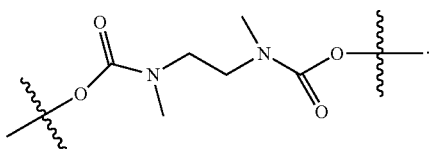 [SMILES: *OC(=O)N(C)CCN(C)C(=O)O*]

In such embodiments, R2 and R3 are conjugated via an attachment comprising a triazole ring (e.g., via a 1,3 cycloaddition reaction).

In some embodiments represented by the formula: R1-R2-R3 (wherein R1 is SN-38, R2 is indolequinone, R3 is c(RGDyK), R1 and R2 and conjugated via a linker represented by

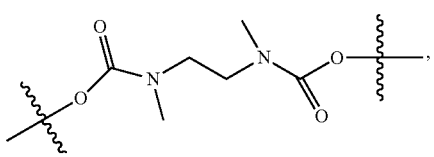 [SMILES: *OC(=O)N(C)CCN(C)C(=O)O*]

and R2 and R3 are conjugated via an attachment comprising a triazole ring, the pro-drug complex is represented by the following structure:

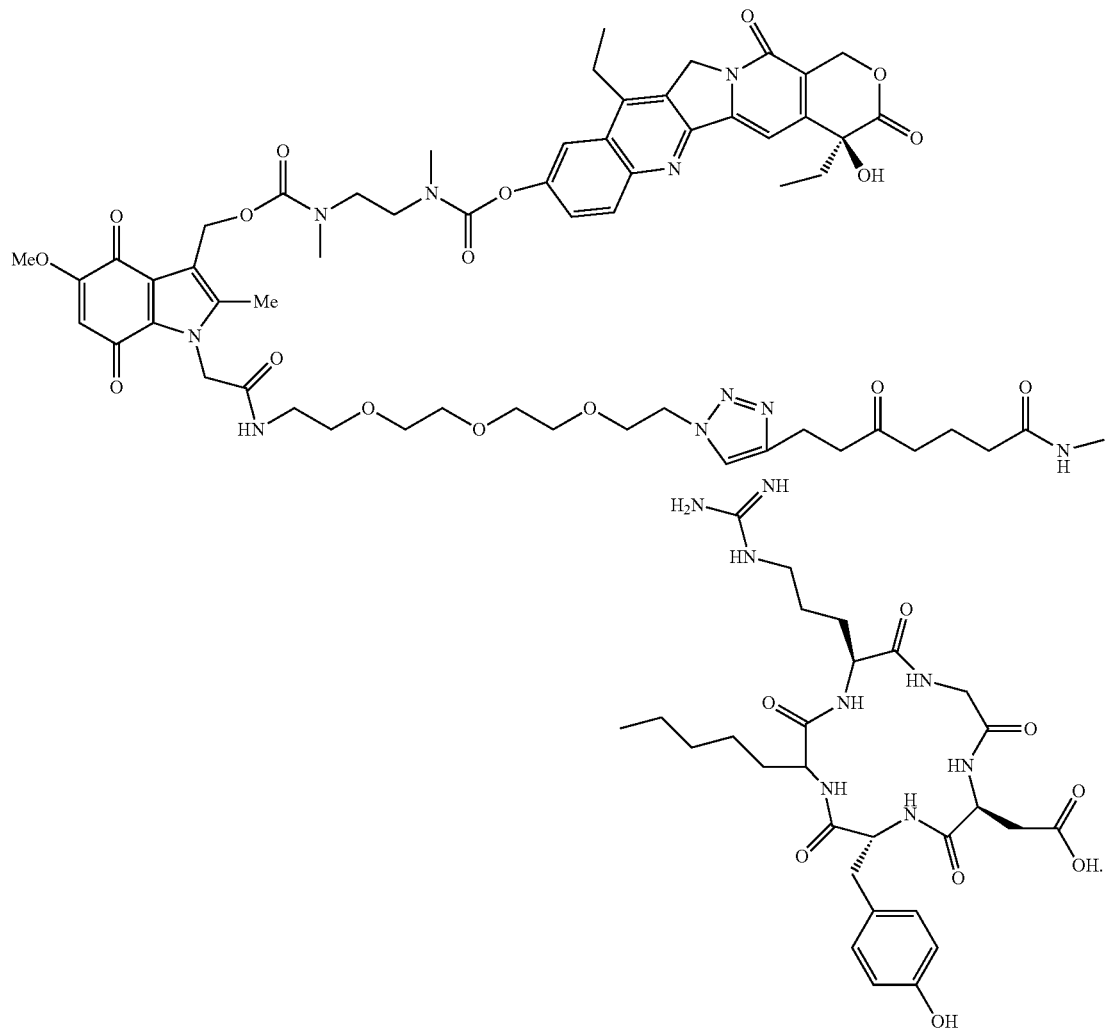

In certain embodiments, the present invention provides methods for treating cancer cells comprising exposing the cancer cells to at least one composition comprising a pro-drug complex of the present invention. In some embodiments, the cancer cells are selected from the group consisting of in vivo, in vitro, and ex vivo. In some embodiments, the cancer cells are in a human.

In certain embodiments, the present invention provides methods for treating cancer in a subject comprising administering to the subject at least one composition comprising a pro-drug complex of the present invention. In some embodiments, the subject is a human.

DEFINITIONS

Figure 1:
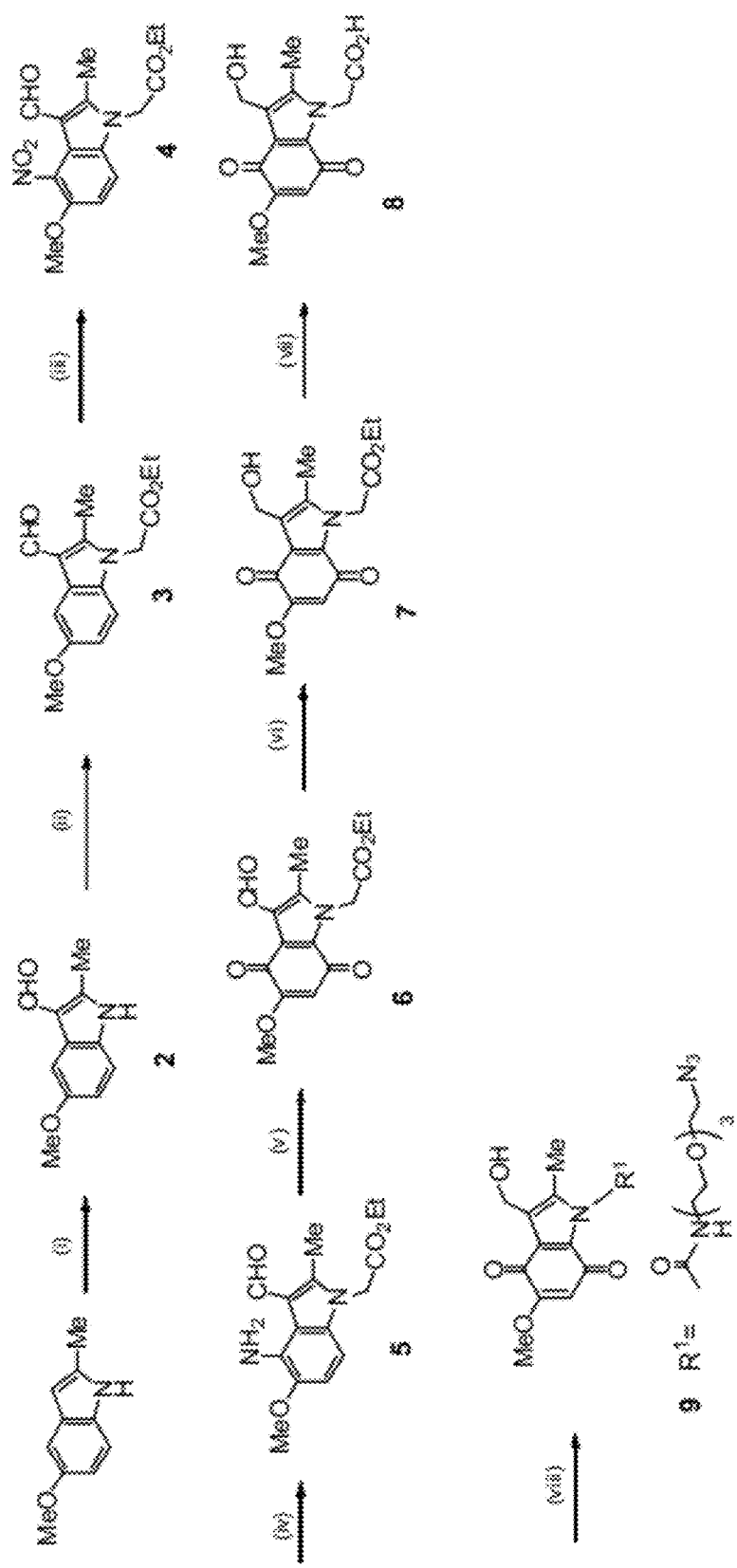
FIG. 1 shows a synthesis scheme for an indolequinone linker.

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests (e.g., PSMA).

As used herein, the term "sample" is used in its broadest sense. In one sense, it is meant to include a specimen or culture obtained from any source; as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "drug" is meant to include any molecule, molecular complex or substance administered to an organism for diagnostic or therapeutic purposes, including medical imaging, monitoring, contraceptive, cosmetic, nutraceutical, pharmaceutical and prophylactic applications. The term "drug" is further meant to include any such molecule, molecular complex or substance that is chemically modified and/or operatively attached to a biologic or biocompatible structure.

As used herein, the term "pro-drug" refers to a drug, drug precursor or modified drug that is not fully active or available until converted in vivo to its therapeutically active or available form.

As used herein, the term "pro-drug complex" refers to a pro-drug conjugated with at least one functional group

DETAILED DESCRIPTION OF THE INVENTION

A prodrug is a pharmacological substance (drug) that is administered in an inactive (or significantly less active) form. Once administered, the prodrug is metabolised in vivo into an active metabolite. The rationale behind the use of a prodrug is generally for absorption, distribution, metabolism, and excretion (ADME) optimization. Prodrugs are usually designed to improve oral bioavailability, with poor absorption from the gastrointestinal tract usually being the limiting factor.

Additionally, the use of a prodrug strategy increases the selectivity of the drug for its intended target. An example of this can be seen in many chemotherapy treatments, in which the reduction of adverse effects is always of paramount importance. Drugs used to target hypoxic cancer cells, through the use of redox-activation, utilise the large quantities of reductase enzyme present in the hypoxic cell to convert the drug into its cytotoxic form, essentially activating it. As the prodrug has low cytotoxicity prior to this activation, there is a markedly lower chance of it "attacking" healthy, non-cancerous cells which reduces the side-effects associated with these chemotherapeutic agents.

In experiments conducted during the course of developing embodiments for the present invention, pro-drug complexes containing functional components were developed having a therapeutic agent (e.g., a chemotherapeutic agent) conjugated with one or more functional groups (e.g., a trigger agent (e.g., for release under hypoxic conditions), and a targeting agent (e.g., a targeting agent specific for $\alpha_v\beta_3$ integrin)). The present invention synthesized camptothecin (or camptothecin based derivative) pro-drug complexes having functional groups. In particular, pro-drug complexes were synthesized with the camptothecin derivative SN-38 conjugated with a trigger agent (e.g., an indolequinone structure for hypoxia triggered drug release) and a targeting agent (e.g., c(RGDyK) for targeting the $\alpha_v\beta_3$ integrin). The SN-38 pro-drug complexes demonstrated high water solubility (e.g., the SN-38 prodrug complex demonstrated solubility greater than or equal to 50 times the solubility of SN-38) (e.g., the SN-38 pro-drug complex demonstrated a solubility of 100 micro gram per milliliter of water versus about 2 micro gram per milliliter for SN38), triple tumor specificity (e.g., hypoxia, DT-Diaphorase, and $\alpha_v\beta_3$ integrin), and prolonged systemic circulation time. Moreover, the SN-38 pro-drug complexes were shown to inhibit cancer cell growth.

Accordingly, the present invention provides methods, compositions and applications for efficient, site-specific drug delivery using pro-drug complexes comprising therapeutic agents conjugated with one or more functional groups (e.g., imaging agents, targeting agents, and trigger agents). In particular, the present invention relates to pro-drug complexes comprising one or more functional groups conjugated with a therapeutic agent (e.g., a chemotherapeutic agent), methods of synthesizing the same, as well as systems and methods utilizing the therapeutic and diagnostic compositions (e.g., in diagnostic and/or therapeutic settings (e.g., for the delivery of therapeutics, imaging, and/or targeting agents (e.g., in disease (e.g., cancer) diagnosis and/or therapy, etc.)). For example, in some embodiments, the novel therapeutic and diagnostic compositions comprise a therapeutic agent (e.g., a chemotherapeutic agent (e.g., camptothecin or a derivative thereof) conjugated with a trigger agent (e.g., for release under hypoxic conditions), and a targeting agent (e.g., a targeting agent specific for $\alpha_v\beta_3$ integrin). As described in more detail below, examples of functional groups include, but are not limited to, targeting groups, trigger groups, and imaging groups.

In some embodiments, therapeutic agent is conjugated to a trigger agent. The present invention is not limited to particular types or kinds of trigger agents.

In some embodiments, sustained release (e.g., slow release over a period of 24-48 hours) of the therapeutic agent is accomplished through conjugating the therapeutic agent (e.g., directly) (e.g., indirectly through one or more additional functional groups) to a trigger agent that slowly degrades in a biological system (e.g., amide linkage, ester linkage, ether linkage). In some embodiments, constitutively active release of the therapeutic agent is accomplished through conjugating the therapeutic agent to a trigger agent that renders the therapeutic agent constitutively active in a biological system (e.g., amide linkage, ether linkage).

In some embodiments, release of the therapeutic agent under specific conditions is accomplished through conjugating the therapeutic agent (e.g., directly) (e.g., indirectly through one or more additional functional groups) to a trigger agent that degrades under such specific conditions (e.g., through activation of a trigger molecule under specific conditions that leads to release of the therapeutic agent). For example, once a conjugate (e.g., a therapeutic agent conjugated with a trigger agent and a targeting agent) arrives at a target site in a subject (e.g., a tumor, or a site of inflammation), components in the target site (e.g., a tumor associated factor, or an inflammatory or pain associated factor) interact with the trigger agent thereby initiating cleavage of the therapeutic agent from the trigger agent. In some embodiments, the trigger agent is configured to degrade (e.g., release the therapeutic agent) upon exposure to a tumor associated factor (e.g., hypoxia and pH, an enzyme (e.g., glucuronidase and/or plasmin), a cathepsin, a matrix metalloproteinase, a hormone receptor (e.g., integrin receptor, hyaluronic acid receptor, luteinizing hormone-releasing hormone receptor, etc.), cancer and/or tumor specific DNA sequence), an inflammatory associated factor (e.g., chemokine, cytokine, etc.) or other moiety.

In some embodiments, the present invention provides a therapeutic agent conjugated with a trigger agent that is sensitive to (e.g., is cleaved by) hypoxia (e.g., indolequinone). Hypoxia is a feature of several disease states, including cancer, inflammation and rheumatoid arthritis, as well as an indicator of respiratory depression (e.g., resulting from analgesic drugs).

Advances in the chemistry of bioreductive drug activation have led to the design of various hypoxia-selective drug delivery systems in which the pharmacophores of drugs are masked by reductively cleaved groups. In some embodiments, the trigger agent is utilizes a quinone, N-oxide and/or (hetero)aromatic nitro groups. For example, a quinone present in a conjugate of the present invention is reduced to phenol under hypoxia conditions, with spontaneous formation of lactone that serves as a driving force for drug release. In some embodiments, a heteroaromatic nitro compound present in a conjugate of the present invention (e.g., a therapeutic agent conjugated (e.g., directly or indirectly) with a trigger agent) is reduced to either an amine or a hydroxylamine, thereby triggering the spontaneous release of a therapeutic agent. In some embodiments, the trigger agent degrades upon detection of reduced pO2 concentrations (e.g., through use of a re-dox linker).

The concept of pro-drug systems in which the pharmacophores of drugs are masked by reductively cleavable groups has been widely explored by many research groups and pharmaceutical companies (see, e.g., Beall, H. D., et al., Journal of Medicinal Chemistry, 1998. 41(24): p. 4755-4766; Ferrer, S., D. P. Naughton, and M. D. Threadgill, Tetrahedron, 2003. 59(19): p. 3445-3454; Naylor, M. A., et al., Journal of Medicinal Chemistry, 1997. 40(15): p. 2335-2346; Phillips, R. M., et al., Journal of Medicinal Chemistry, 1999. 42(20): p. 4071-4080; Zhang, Z., et al., Organic & Biomolecular Chemistry, 2005. 3(10): p. 1905-1910; each of which are herein incorporated by reference in their entireties). Several such hypoxia activated pro-drugs have been advanced to clinical investigations, and work in relevant oxygen concentrations to prevent cerebral damage. The present invention is not limited to particular hypoxia activated trigger agents. In some embodiments, the hypoxia activated trigger agents include, but are not limited to, indolequinones, nitroimidazoles, and nitroheterocycles (see, e.g., Damen, E. W. P., et al., Bioorganic & Medicinal Chemistry, 2002. 10(1): p. 71-77; Hay, M. P., et al., Journal of Medicinal Chemistry, 2003. 46(25): p. 5533-5545; Hay, M. P., et al., Journal of the Chemical Society-Perkin Transactions 1, 1999(19): p. 2759-2770; each herein incorporated by reference in their entireties). In experiments conducted during the course of developing embodiments for the present invention, pro-drug complexes were synthesized with the camptothecin derivative SN-38 conjugated with a trigger agent (e.g., an indolequinone structure for hypoxia triggered drug release) and a targeting agent (e.g., c(RGDyK) for targeting the $\alpha_v\beta_3$ integrin). The SN-38 pro-drug complexes demonstrated high water solubility, triple tumor specificity (e.g., hypoxia, DT-Diaphorase, and $\alpha_v\beta_3$ integrin), and prolonged systemic circulation time.

In some embodiments, the trigger agent is sensitive to (e.g., is cleaved by) and/or associates with a tumor associated enzyme. For example, in some embodiments, the trigger agent that is sensitive to (e.g., is cleaved by) and/or associates with a glucuronidase. Glucuronic acid can be attached to several anticancer drugs via various linkers. These anticancer drugs include, but are not limited to, doxorubicin, paclitaxel, docetaxel, 5-fluorouracil, 9-aminocamtothecin, as well as other drugs under development. These pro-drugs are generally stable at physiological pH and are significantly less toxic than the parent drugs.

In some embodiments, the trigger agent is sensitive to (e.g., is cleaved by) and/or associates with brain enzymes. For example, trigger agents such as indolequinone are reduced by brain enzymes such as, for example, diaphorase (DT-diaphorase) (see, e.g., Damen, E. W. P., et al., Bioorganic & Medicinal Chemistry, 2002. 10(1): p. 71-77; herein incorporated by reference in its entirety). For example, in such embodiments, the antagonist is only active when released during hypoxia to prevent respiratory failure.

In some embodiments, the trigger agent is sensitive to (e.g., is cleaved by) and/or associates with a protease. The present invention is not limited to any particular protease. In some embodiments, the protease is a cathepsin. In some embodiments, a trigger comprises a Lys-Phe-PABC moiety (e.g., that acts as a trigger). In some embodiments, a Lys-Phe-PABC moiety linked to doxorubicin, mitomycin C, and paclitaxel are utilized as a trigger-therapeutic conjugate in a dendrimer conjugate provided herein (e.g., that serve as substrates for lysosomal cathepsin B or other proteases expressed (e.g., overexpressed) in tumor cells. In some embodiments, utilization of a 1,6-elimination spacer/linker is utilized (e.g., to permit release of therapeutic drug post activation of trigger).

In some embodiments, the trigger agent is sensitive to (e.g., is cleaved by) and/or associates with plasmin. The serine protease plasmin is over expressed in many human tumor tissues. Tripeptide specifiers (e.g., including, but not limited to, Val-Leu-Lys) have been identified and linked to anticancer drugs through elimination or cyclization linkers.

In some embodiments, the trigger agent is sensitive to (e.g., is cleaved by) and/or associates with a matrix metalloproteases (MMPs). In some embodiments, the trigger agent is sensitive to (e.g., is cleaved by) and/or that associates with β-Lactamase (e.g., a β-Lactamase activated cephalosporin-based pro-drug).

In some embodiments, the trigger agent is sensitive to (e.g., is cleaved by) and/or activated by a receptor (e.g., expressed on a target cell (e.g., a tumor cell)).

In some embodiments, the trigger agent that is sensitive to (e.g., is cleaved by) and/or activated by a nucleic acid. Nucleic acid triggered catalytic drug release can be utilized in the design of chemotherapeutic agents. Thus, in some embodiments, disease specific nucleic acid sequence is utilized as a drug releasing enzyme-like catalyst (e.g., via complex formation with a complimentary catalyst-bearing nucleic acid and/or analog). In some embodiments, the release of a therapeutic agent is facilitated by the therapeutic component being attached to a labile protecting group, such as, for example, cisplatin or methotrexate being attached to a photolabile protecting group that becomes released by laser light directed at cells emitting a color of fluorescence (e.g., in addition to and/or in place of target activated activation of a trigger component of a dendrimer conjugate). In some embodiments, the therapeutic device also may have a component to monitor the response of the tumor to therapy. For example, where a therapeutic agent of the dendrimer induces apoptosis of a target cell (e.g., a cancer cell (e.g., a prostate cancer cell)), the caspase activity of the cells may be used to activate a green fluorescence. This allows apoptotic cells to turn orange, (combination of red and green) while residual cells remain red. Any normal cells that are induced to undergo apoptosis in collateral damage fluoresce green.

In some embodiments, therapeutic agent is conjugated (e.g., directly or indirectly) to a targeting agent. The present invention is not limited to any particular targeting agent. In some embodiments, targeting agents are conjugated to the therapeutic agents for delivery of the therapeutic agents to desired body regions (e.g., to the central nervous system (CNS); to a tumor). The targeting agents are not limited to targeting specific body regions.

In some embodiments, the targeting agent is a moiety that has affinity for a tumor associated factor. For example, a number of targeting agents are contemplated to be useful in the present invention including, but not limited to, RGD sequences, low-density lipoprotein sequences, a NAALADase inhibitor, epidermal growth factor, and other agents that bind with specificity to a target cell (e.g., a cancer cell)).

For example, the present invention provides pro-drug complexes with the camptothecin derivative SN-38 conjugated with c(RGDyK) as a targeting agent. Arg-Gly-Asp(RGD) has high affinity for $\alpha_v\beta_3$ selective ligands, and the $\alpha_v\beta_3$ integrin is a specific and unique marker that differentiates newly formed capillaries from their mature counterparts. Accordingly, the pro-drug complexes of the present invention utilizing RGD as a targeting agent are able to target tumor cells with newly forming capillaries. In particular, pro-drug complexes synthesized with the camptothecin derivative SN-38 conjugated with a trigger agent (e.g., an indolequinone structure for hypoxia triggered drug release) and a targeting agent (e.g., c(RGDyK) for targeting the $\alpha_v\beta_3$ integrin) demonstrated high water solubility, triple tumor specificity (e.g., hypoxia, DT-Diaphorase, and $\alpha_v\beta_3$ integrin), and prolonged systemic circulation time.

The present invention is not limited to cancer and/or tumor targeting agents. Indeed, pro-drug complexes of the present invention can be targeted (e.g., via a linker conjugated to the dendrimer wherein the linker comprises a targeting agent) to a variety of target cells or tissues (e.g., to a biologically relevant environment) via conjugation to an appropriate targeting agent. For example, in some embodiments, the targeting agent is a moiety that has affinity for an inflammatory factor (e.g., a cytokine or a cytokine receptor moiety (e.g., TNF-α receptor)). In some embodiments, the targeting agent is a sugar, peptide, antibody or antibody fragment, hormone, hormone receptor, or the like.

In some embodiments of the present invention, the targeting agent includes, but is not limited to an antibody, receptor ligand, hormone, vitamin, and antigen, however, the present invention is not limited by the nature of the targeting agent. In some embodiments, the antibody is specific for a disease-specific antigen. In some embodiments, the disease-specific antigen comprises a tumor-specific antigen. In some embodiments, the receptor ligand includes, but is not limited to, a ligand for CFTR, EGFR, estrogen receptor, FGR2, folate receptor, IL-2 receptor, glycoprotein, and VEGFR. In some embodiments, the receptor ligand is folic acid.

Antibodies can be generated to allow for the targeting of antigens or immunogens (e.g., tumor, tissue or pathogen specific antigens) on various biological targets (e.g., pathogens, tumor cells, normal tissue). Such antibodies include, but are not limited to polyclonal, monoclonal, chimeric, single chain, Fab fragments, and an Fab expression library.

In some embodiments, the targeting agent is an antibody. In some embodiments, the antibodies recognize, for example, tumor specific epitopes (e.g., TAG-72 (See, e.g., Kjeldsen et al., Cancer Res. 48:2214-2220 (1988); U.S. Pat. Nos. 5,892,020; 5,892,019; and 5,512,443; each herein incorporated by reference in their entireties); human carcinoma antigen (See, e.g., U.S. Pat. Nos. 5,693,763; 5,545,530; and 5,808,005; each herein incorporated by reference in their entireties); TP1 and TP3 antigens from osteocarcinoma cells (See, e.g., U.S. Pat. No. 5,855,866; herein incorporated by reference in its entirety); Thomsen-Friedenreich (TF) antigen from adenocarcinoma cells (See, e.g., U.S. Pat. No. 5,110,911; herein incorporated by reference in its entirety); "KC-4 antigen" from human prostate adenocarcinoma (See, e.g., U.S. Pat. Nos. 4,708,930 and 4,743,543; each herein incorporated by reference in their entireties); a human colorectal cancer antigen (See, e.g., U.S. Pat. No. 4,921,789; herein incorporated by reference in its entirety); CA125 antigen from cystadenocarcinoma (See, e.g., U.S. Pat. No. 4,921,790; herein incorporated by reference in its entirety); DF3 antigen from human breast carcinoma (See, e.g., U.S. Pat. Nos. 4,963,484 and 5,053,489; each herein incorporated by reference in their entireties); a human breast tumor antigen (See, e.g., U.S. Pat. No. 4,939,240: herein incorporated by reference in its entirety); p97 antigen of human melanoma (See, e.g., U.S. Pat. No. 4,918,164: herein incorporated by reference in its entirety); carcinoma or orosomucoid-related antigen (CORA) (See, e.g., U.S. Pat. No. 4,914,021; herein incorporated by reference in its entirety); a human pulmonary carcinoma antigen that reacts with human squamous cell lung carcinoma but not with human small cell lung carcinoma (See, e.g., U.S. Pat. No. 4,892,935; herein incorporated by reference in its entirety); T and Tn haptens in glycoproteins of human breast carcinoma (See, e.g., Springer et al., Carbohydr. Res. 178:271-292 (1988); herein incorporated by reference in its entirety), MSA breast carcinoma glycoprotein termed (See, e.g., Tjandra et al., Br. J. Surg. 75:811-817 (1988); herein incorporated by reference in its entirety); MFGM breast carcinoma antigen (See, e.g., Ishida et al., Tumor Biol. 10:12-22 (1989); herein incorporated by reference in its entirety); DU-PAN-2 pancreatic carcinoma antigen (See, e.g., Lan et al., Cancer Res. 45:305-310 (1985); herein incorporated by reference in its entirety); CA125 ovarian carcinoma antigen (See, e.g., Hanisch et al., Carbohydr. Res. 178:29-47 (1988); herein incorporated by reference in its entirety); YH206 lung carcinoma antigen (See, e.g., Hinoda et al., (1988) Cancer J. 42:653-658 (1988); herein incorporated by reference in its entirety).

In some embodiments, the targeting agents target the central nervous system (CNS). In some embodiments, where the targeting agent is specific for the CNS, the targeting agent is transferrin (see, e.g., Daniels, T. R., et al., Clinical Immunology, 2006. 121(2): p. 159-176; Daniels, T. R., et al., Clinical Immunology, 2006. 121(2): p. 144-158; each herein incorporated by reference in their entireties). Transferrin has been utilized as a targeting vector to transport, for example, drugs, liposomes and proteins across the BBB by receptor mediated transcytosis (see, e.g., Smith, M. W. and M. Gumbleton, Journal of Drug Targeting, 2006. 14(4): p. 191-214; herein incorporated by reference in its entirety). In some embodiments, the targeting agents target neurons within the central nervous system (CNS). In some embodiments, where the targeting agent is specific for neurons within the CNS, the targeting agent is a synthetic tetanus toxin fragment (e.g., a 12 amino acid peptide (Tet 1) (HLNILSTLWKYR) (SEQ ID NO:2)) (see, e.g., Liu, J. K., et al., Neurobiology of Disease, 2005. 19(3): p. 407-418; herein incorporated by reference in its entirety).

In some embodiments, therapeutic agent is conjugated (e.g., directly or indirectly) to an imaging agent. A multiplicity of imaging agents find use in the present invention. In some embodiments, a pro-drug complex (e.g., a therepatuic conjugated with at least one functional group) comprises at least one imaging agent that can be readily imaged. The present invention is not limited by the nature of the imaging component used. In some embodiments of the present invention, imaging modules comprise surface modifications of quantum dots (See e.g., Chan and Nie, Science 281:2016 (1998)) such as zinc sulfide-capped cadmium selenide coupled to biomolecules (Sooklal, Adv. Mater., 10:1083 (1998)).

In some embodiments, once a targeted pro-drug complex has attached to (or been internalized into) a target cell (e.g., tumor cell and or inflammatory cell), one or more modules on the pro-drug serve to image its location. In some embodiments, chelated paramagnetic ions, such as Gd(III)-diethylenetriaminepentaacetic acid (Gd(III)-DTPA), are conjugated to the pro-drug complex. Other paramagnetic ions that may be useful in this context include, but are not limited to, gadolinium, manganese, copper, chromium, iron, cobalt, erbium, nickel, europium, technetium, indium, samarium, dysprosium, ruthenium, ytterbium, yttrium, and holmium ions and combinations thereof.

Dendrimeric gadolinium contrast agents have even been used to differentiate between benign and malignant breast tumors using dynamic MRI, based on how the vasculature for the latter type of tumor images more densely (Adam et al., Ivest. Rad. 31:26 (1996)). Thus, MRI provides a particularly useful imaging system of the present invention.

Pro-drug complexes of the present invention allow functional microscopic imaging of tumors and provide improved methods for imaging. The methods find use in vivo, in vitro, and ex vivo. For example, in one embodiment of the present invention, pro-drug complexes of the present invention are designed to emit light or other detectable signals upon exposure to light. Although the labeled pro-drug complexes may be physically smaller than the optical resolution limit of the microscopy technique, they become self-luminous objects when excited and are readily observable and measurable using optical techniques. In some embodiments of the present invention, sensing fluorescent biosensors in a microscope involves the use of tunable excitation and emission filters and multiwavelength sources (See, e.g., Farkas et al., SPEI 2678: 200 (1997); herein incorporated by reference in its entirety). In embodiments where the imaging agents are present in deeper tissue, longer wavelengths in the Near-infrared (NMR) are used (See e.g., Lester et al., Cell Mol. Biol. 44:29 (1998); herein incorporated by reference in its entirety). Biosensors that find use with the present invention include, but are not limited to, fluorescent dyes and molecular beacons.

In some embodiments of the present invention, in vivo imaging is accomplished using functional imaging techniques. Functional imaging is a complementary and potentially more powerful techniques as compared to static structural imaging. Functional imaging is best known for its application at the macroscopic scale, with examples including functional Magnetic Resonance Imaging (fMRI) and Positron Emission Tomography (PET). However, functional microscopic imaging may also be conducted and find use in in vivo and ex vivo analysis of living tissue. Functional microscopic imaging is an efficient combination of 3-D imaging, 3-D spatial multispectral volumetric assignment, and temporal sampling: in short a type of 3-D spectral microscopic movie loop. Interestingly, cells and tissues autofluoresce. When excited by several wavelengths, providing much of the basic 3-D structure needed to characterize several cellular components (e.g., the nucleus) without specific labeling. Oblique light illumination is also useful to collect structural information and is used routinely. As opposed to structural spectral microimaging, functional spectral microimaging may be used with biosensors, which act to localize physiologic signals within the cell or tissue. For example, in some embodiments of the present invention, biosensor-comprising pro-drug complexes of the present invention are used to image upregulated receptor families such as the folate or EGF classes. In such embodiments, functional biosensing therefore involves the detection of physiological abnormalities relevant to carcinogenesis or malignancy, even at early stages. A number of physiological conditions may be imaged using the compositions and methods of the present invention including, but not limited to, detection of nanoscopic biosensors for pH, oxygen concentration, $Ca^{2+}$ concentration, and other physiologically relevant analytes.

In some embodiments, the present invention provides pro-drug complexes having a biological monitoring component. The biological monitoring or sensing component of a pro-drug complex of the present invention is one that can monitor the particular response in a target cell (e.g., tumor cell) induced by an agent (e.g., a therapeutic agent provided by the pro-drug complex). While the present invention is not limited to any particular monitoring system, the invention is illustrated by methods and compositions for monitoring cancer treatments. In preferred embodiments of the present invention, the agent induces apoptosis in cells and monitoring involves the detection of apoptosis. In some embodiments, the monitoring component is an agent that fluoresces at a particular wavelength when apoptosis occurs. For example, in a preferred embodiment, caspase activity activates green fluorescence in the monitoring component. Apoptotic cancer cells, which have turned red as a result of being targeted by a particular signature with a red label, turn orange while residual cancer cells remain red. Normal cells induced to undergo apoptosis (e.g., through collateral damage), if present, will fluoresce green.

In these embodiments, fluorescent groups such as fluorescein are employed in the imaging agent. Fluorescein is easily attached to the dendrimer surface via the isothiocyanate derivatives, available from MOLECULAR PROBES, Inc. This allows the pro-drug complex to be imaged with the cells via confocal microscopy. Sensing of the effectiveness of the pro-drug complexes is preferably achieved by using fluorogenic peptide enzyme substrates. For example, apoptosis caused by the therapeutic agent results in the production of the peptidase caspase-1 (ICE). CALBIOCHEM sells a number of peptide substrates for this enzyme that release a fluorescent moiety. A particularly useful peptide for use in the present invention is: MCA-Tyr-Glu-Val-Asp-Gly-Trp-Lys-(DNP)-NH$_2$ (SEQ ID NO: 1) where MCA is the (7-methoxycoumarin-4-yl)acetyl and DNP is the 2,4-dinitrophenyl group (See, e.g., Talanian et al., J. Biol. Chem., 272: 9677 (1997); herein incorporated by reference in its entirety). In this peptide, the MCA group has greatly attenuated fluorescence, due to fluorogenic resonance energy transfer (FRET) to the DNP group. When the enzyme cleaves the peptide between the aspartic acid and glycine residues, the MCA and DNP are separated, and the MCA group strongly fluoresces green (excitation maximum at 325 nm and emission maximum at 392 nm). In some embodiments, the lysine end of the peptide is linked to pro-drug complex, so that the MCA group is released into the cytosol when it is cleaved. The lysine end of the peptide is a useful synthetic handle for conjugation because, for example, it can react with the activated ester group of a bifunctional linker such as Mal-PEG-OSu. Thus the appearance of green fluorescence in the target cells produced using these methods provides a clear indication that apoptosis has begun (if the cell already has a red color from the presence of aggregated quantum dots, the cell turns orange from the combined colors).

Additional fluorescent dyes that find use with the present invention include, but are not limited to, acridine orange, reported as sensitive to DNA changes in apoptotic cells (see, e.g., Abrams et al., Development 117:29 (1993); herein incorporated by reference in its entirety) and cis-parinaric acid, sensitive to the lipid peroxidation that accompanies apoptosis (see, e.g., Hockenbery et al., Cell 75:241 (1993); herein incorporated by reference in its entirety). It should be noted that the peptide and the fluorescent dyes are merely exemplary. It is contemplated that any peptide that effectively acts as a substrate for a caspase produced as a result of apoptosis finds use with the present invention.

The present invention is not limited by the type of therapeutic agent delivered via the pro-drug complex of the present invention. For example, a therapeutic agent may be any agent selected from the group comprising, but not limited to, a pain relief agent, a pain relief agent antagonist, a chemotherapeutic agent, an anti-oncogenic agent, an anti-angiogenic agent, a tumor suppressor agent, an anti-microbial agent, or an expression construct comprising a nucleic acid encoding a therapeutic protein.

In some embodiments, the therapeutic agent comprises a compound of the camptothecin family (e.g., IRINOTECAN). Camptothecin (CPT)

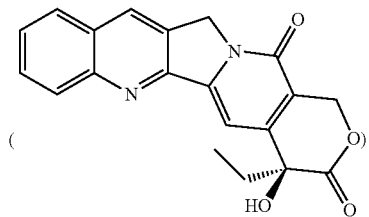

is a cytotoxic quinoline alkaloid which inhibits the DNA enzyme topoisomerase I (topo I). It was discovered in 1966 by M. E. Wall and M. C. Wani in systematic screening of natural products for anticancer drugs. It was isolated from the bark and stem of *Camptotheca Acuminata* (*Camptotheca*, Happy tree), a tree native in China. CPT showed remarkable anticancer activity in preliminary clinical trials but also low solubility and adverse drug reaction. Because of these disadvantages researchers have made numbers of derivatives to increase the benefits of the chemical. Two CPT analogues have been approved and are used in cancer chemotherapy today, topotecan and irinotecan (see, e.g., M. E. Wall, et al., 1966 J. Am. Chem. Soc 88: 3888-3890; G. Samuelsson, 2004, Drugs of Natural Origin: a Textbook of Pharmacology (5 ed.); each herein incorporated by reference in their entireties).

CPT has a planar pentacyclic ring structure, that includes a pyrrolo[3,4-β]-quinoline moiety (rings A, B and C), conjugated pyridone moiety (ring D) and one chiral center at position 20 within the alpha-hydroxy lactone ring with (S) configuration (the E-ring)

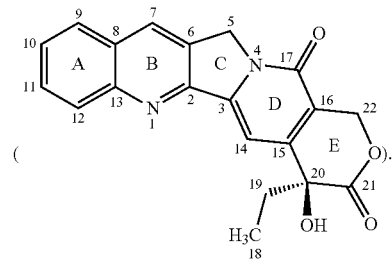

Its planar structure is thought to be one of the most important factors in topoisomerase inhibition (see, e.g., H. Ulukan, et al., 2002, Drugs 62 (2): 2039-2057; A. J. Lu, 2007, European Journal of Medicinal Chemistry 42 (4): 307-314; each herein incorporated by reference in their entireties).

CPT binds to the topo I and DNA complex (the covalent complex) resulting in a ternary complex, and thereby stabilizing it. This prevents DNA re-ligation and therefore causes DNA damage which results in apoptosis. CPT binds both to the enzyme and DNA with hydrogen bonds. An important part of the structure is the E-ring which interacts from three different positions with the enzyme. The hydroxyl group in position 20 forms hydrogen bond to the side chain on aspartic acid number 533 (Asp533) in the enzyme. It's critical that the configuration of the chiral carbon is (S) because (R) is inactive. The lactone is bonded with two hydrogen bonds to the amino groups on arginine 364 (Arg364). The D-ring interacts with the +1 cytosine on non-cleaved strand and stabilizes the topo I-DNA covalent complex by forming hydrogen bond. This hydrogen bond is between carbonyl group in position 17 on the D-ring and amino group on the pyrimidine ring of +1 cytosine (see, e.g., D. J. Adams, et al., 2005, Cancer Chemotherapy and Pharmacology 57 (2): 145-154; M. R. Redinbo, 1998, Science 279: 1504-1513; each herein incorporated by reference in their entireties). Toxicity of CPT is primarily a result of conversion of single-strand breaks into double-strand breaks during the S-phase when the replication fork collides with the cleavage complexes formed by DNA and CPT (see, e.g., Y. Pommier, et al., 2003, Mutat. Res. 532: 173-203; herein incorporated by reference in its entirety).

The lactone ring in CPT is highly susceptible to hydrolysis. The open ring form is inactive and it must therefore by closed to inhibit topo I. The closed form is favored in acidic condition, as it is in many cancer cells microenvironment. CPT is transported in to the cell by passive diffusion. Cellular uptake is favored by lipophilicity, which enhances intracellular accumulation. Lipophilicity makes compounds more stable because of improved lactone partitioning into red blood cells and consequently less hydrolysis of the lactone. CPT has affinity for human serum albumin (HSA), especially the carboxylate form of CPT. Because of that, the equilibrium between the lactone ring and the carboxylate form is driven toward the carboxylate. Reduced drug-HSA interactions could result in improved activity (see, e.g., D. J. Adams, 2005, Cancer Chemotherapy and Pharmacology 57 (2): 145-154; F. Zunino, 2002, Current Pharmaceutical Design 8: 2505-2520; each herein incorporated by reference in their entireties).

In some embodiments, the therapeutic agent is a derivative of camptothecin. The present invention is not limited to a particular type of camptothecin derivative. In some embodiments, the camptothecin derivative comprises a substitution at position 7, 9, 10 and/or 11. In some embodiments, the camptothecin derivative comprises an enlargement of the lactone ring by one methylene unit (e.g., homocamptothecin).

In some embodiments, the camptothecin derivative comprises an alkyl substitution at position 7 (e.g., ethyl ($C_2H_5$) or chloromethyl ($CH_2Cl$)). Ethyl ($C_2H_5$) or chloromethyl ($CH_2Cl$) are able to react with the DNA in the presence of topo 1 which leads to more tumor activity. In some embodiments, the camptothecin derivative comprises increased length of the carbon chain (in position 7) so as to increase lipophilicity and consequently greater potency and stability in human plasma (see, e.g., D. J. Adams, 2005, Cancer Chemotherapy and Pharmacology 57 (2): 145-154; F. Zunino, 2002, Current Pharmaceutical Design 8: 2505-2520; each herein incorporated by reference in their entireties). In some embodiments, the camptothecin derivative include silatecans and karenitecins. Silatecans and karenitecins are potent inihibitors on topo I and both have alkylsilyl groups in position 7 which make them lipophilic and more stable. Silatecans or 7-silylcampthothecins have shown reduced drug-HSA interactions which contributes to its blood stability and they can also cross the blood brain barrier. DB-67 is a 10-hydroxy derivative and is an active silatecan. BNP1350 which belongs to the series of karenitecins exhibits cytotoxic activity and ability to overcome drug resistance. In some embodiments, the camptothecin derivative involves introduction of lipophilic substituents, such as iminomethyl or oxyiminomethyl moieties. A potent compound is the oxyiminomethyl derivative ST1481 that has the advantage to overcome drug resistance caused by transport systems (see, e.g., F. Zunino, 2002, Current Pharmaceutical Design 8: 2505-2520; herein incorporated by reference in its entirety). Basic nitrogen in a carbon chain at position 7 makes the compound more hydrophilic and hence more water-soluble. In some embodiments, the camptothecin derivative is CKD-602, which is a potent topo I inhibitor and successfully overcomes the poor water solubility and toxicity seen with CPT (see, e.g., F. Zunino, 2002, Current Pharmaceutical Design 8: 2505-2520; M. K. Chung, 2006, Regulatory Toxicology and Pharmacology 45 (3): 273-281; each herein incorporated by reference in their entireties). In some embodiments, the camptothecin derivative has electron-withdrawing groups (e.g., amino, nitro, bromo or chloro) at position 9 and 10 and a hydroxyl group at position 10 or 11.

In some embodiments, the camptothecin derivative is a hexacyclic camptothecin analogue. For example, in some embodiments, the camptothecin derivative comprises a methylenedioxy or ethylenedioxy group connected between 10 and 11 thereby forming a 5 or 6 membered ring which leads, for example, to more water-soluble derivates and increased potency. In some embodiments, the camptothecin derivative comprises an amino or chloro group at the 9th position or a chloromethyl group at the 7th position to 10,11-methylenedioxy or ethylenedioxy analogues. In some embodiments, the camptothecin derivative comprises a ring configuration formed between position 7 and 9 (e.g., position 10 and 11). In some embodiments, the hexacyclic CPT has thereon electron-withdrawing groups at position 11 and methyl or amino groups at 10. In some embodiments, the camptothecin derivative is Exatecan (e.g., a 6 membered ring over position 7 and 9, and is 10-methyl, 11-fluoro substituted) (see, e.g., A. J. Lu, et al., 2007, European Journal of Medicinal Chemistry 42 (4): 307-314; herein incorporated by reference in its entirety).

In some embodiments, the camptothecin derivative is shown by the following formula:

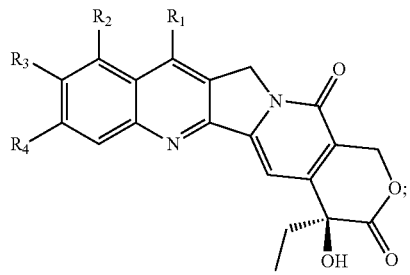

wherein R1, R2, R3 and R4 are described in Table 1.

TABLE 1

| Analogue | R1 | R2 | R3 | R4 |
|---|---|---|---|---|
| Topotecan | —H | $CH_2N(CH_3)_2$ | —OH | H |
| Irinotecan | $CH_2CH_3$ | H | [piperidinyl-piperidine carbonyloxy structure] | H |
| DB 67 | [tert-butyldimethylsilyl structure] | H | OH | H |
| BNP 1350 | $CH_2CH_2Si(CH_3)_3$ | H | H | H |
| Exatecan | [aminoalkyl structure with $NH_2$] | | $CH_3$ | F |

TABLE 1-continued

| Analogue | R1 | R2 | R3 | R4 |
|---|---|---|---|---|
| Lurtotecan | —N(piperazine)N— | H | —O—CH₂—CH₂—O— (dioxane) | |
| ST 1481 | CH=NOC(CH$_3$)$_3$ | H | H | H |
| CKD 602 | CH$_2$CH$_2$NHCH(CH$_3$)$_2$ | H | H | H |

In some embodiments, the camptothecin derivative is SN-38:

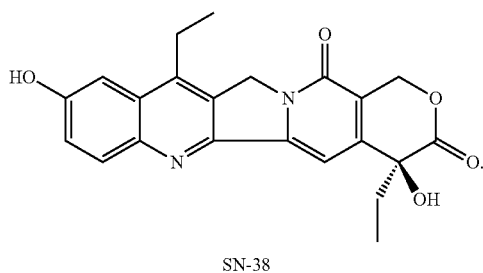 [SMILES: CCc1c2c(nc3ccc(O)cc13)-c1cc3c(c(=O)n1C2)COC(=O)[C@]3(O)CC ; "SN-38"]

SN-38

7-Ethyl-10-hydroxy-camptothecin (SN-38), the active metabolite of the anti-cancer agent irinotecan, contains a lactone ring that equilibrates with a carboxylate form. In experiments conducted during the course of developing embodiments for the present invention, c(RGDyK) targeted SN38 pro-drugs possessing an indolequinone structure for hypoxia triggered drug release were synthesized, and high water solubility, triple tumor specificity (e.g., hypoxia, DT-Diaphorase, and $\alpha_v\beta_3$ integrin), and prolonged systemic circulation time demonstrated.

In some embodiments, the therapeutic agent is an anti-angiogenic agent. Indeed, a variety of anti-angiogenic agents are contemplated including, but not limited to, Batimastat, Marimastat, AG3340, Neovastat, PEX, TIMP-1, -2, -3, -4, PAI-1, -2, uPA Ab, uPAR Ab, Amiloride, Minocycline, tetracyclines, steroids, cartilage-derived TIMP, $\alpha v\beta 3$ Ab: LM609 and Vitaxin, RGD containing peptides, $\alpha v\beta 5$ Ab, Endostatin, Angiostatin, aaAT, IFN-$\alpha$, IFN-$\gamma$, IL-12, nitric oxide synthase inhibitors, TSP-1, TNP-470, Combretastatin A4, Thalidomide, Linomide, IFN-$\alpha$, PF-4, prolactin fragment, Suramin and analogues, PPS, distamycin A analogues, FGF-2 Ab, antisense-FGF-2, Protamine, SU5416, soluble Flt-1, dominant-negative Flk-1, VEGF receptor ribosymes, VEGF Ab, Aspirin, NS-398, 6-AT, 6A5BU, 7-DX, Genistein, Lavendustin A, Ang-2, batimastat, marimastat, anti-$\alpha v\beta 3$ monoclonal antibody (LM609) thrombospondin-1 (TSP-1) Angiostatin, endostatin, TNP-470, Combretastatin A-4, Anti-VEGF antibodies, soluble Flk-1, Flt-1 receptors, inhibitors of tyrosine kinase receptors, SU5416, heparin-binding growth factors, pentosan polysulfate, platelet-derived endothelial cell growth factor/Thymidine phosphorylase (PD-ECGF/TP), cox (e.g., cox-1 an cox-2) inhibitors (e.g., Celebrex and Vioxx), DT385, Tissue inhibitor of metalloprotease (TIMP-1, TIMP-2), Zinc, Plasminogen activator-inhibitor-1 (PAI-1), p53 Rb, Interleukin-10 Interleukin-12, Angiopoietin-2, Angiotensin, Angiotensin II (AT2 receptor), Caveolin-1, caveolin-2, Angiopoietin-2, Angiotensin, Angiotensin 11 (AT2 receptor), Caveolin-1, caveolin-2, Endostatin, Interferon-alpha, Isoflavones, Platelet factor-4, Prolactin (16 Kd fragment), Thrombospondin, Troponin-I, Bay 12-9566, AG3340, CGS 27023A, CGS 27023A, COL-3, (Neovastat), BMS-275291, Penicillamine, TNP-470 (fumagillin derivative), Squalamine, Combretastatin, Endostatin, Penicillamine, Farnesyl Transferase Inhibitor (FTI), -L-778,123, -SCH66336, -R115777, anti-VEGF antibody, Thalidomide, SU5416, Ribozyme, Angiozyme, SU6668, PTK787/ZK22584, Interferon-alpha, Interferon-alpha, Suramin, Vitaxin, EMD121974, Penicillamine, Tetrathiomolybdate, Captopril, serine protease inhibitors, CAI, ABT-627, CM101/ZDO101, Interleukin-12, IM862, PNU-145156E, those described in U.S. Patent App. No. 20050123605, herein incorporated by reference in its entirety, and fragments or portions of the above that retain anti-angiogenic (e.g., angiostatic or inhibitory properties).

In some embodiments, the therapeutic agent is a chemotherapeutic agent. Examples of chemotherapeutic agents include, but are not limited to, platinum complex, verapamil, podophylltoxin, carboplatin, procarbazine, mechloroethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, bleomycin, etoposide, tamoxifen, paclitaxel, taxol, transplatinum, 5-fluorouracil, vincristin, vinblastin, bisphosphonate (e.g., CB3717), chemotherapeutic agents with high affinity for folic acid receptors, ALIMTA (Eli Lilly), and methotrexate.

In some embodiments, the therapeutic agent is an anti-oncogenic agent. In some embodiments, the anti-oncogenic agent comprises an antisense nucleic acid (e.g., RNA, molecule). In certain embodiments, the antisense nucleic acid comprises a sequence complementary to an RNA of an oncogene. In preferred embodiments, the oncogene includes, but is not limited to, abl, Bcl-2, Bcl-xL, erb, fms, gsp, hst, jun, myc, neu, raf; ras, ret, src, or trk. In some embodiments, the nucleic acid encoding a therapeutic protein encodes a factor including, but not limited to, a tumor suppressor, cytokine, receptor, inducer of apoptosis, or differentiating agent. In preferred embodiments, the tumor suppressor includes, but is not limited to, BRCA1, BRCA2, C-CAM, p16, p21, p53, p73, Rb, and p27. In preferred embodiments, the cytokine includes, but is not limited to, GMCSF, IL-1, IL-2, IL-3, IL-4, IL-5, IL-6, IL-7, IL-8; IL-9, IL-10, IL-11, IL-12, IL-13, IL-14, IL-15, $\beta$-interferon, $\gamma$-interferon, and TNF. In preferred embodiments, the receptor includes, but is not limited to, CFTR, EGFR, estrogen receptor, IL-2 receptor, and VEGFR. In preferred embodiments, the inducer of apoptosis includes, but is not limited to, AdE1B, Bad, Bak, Bax, Bid, Bik, Bim, Harakid, and ICE-CED3 protease. In some embodiments, the therapeutic agent comprises a short-half life radioisotope.

The present invention is limited to particular configurations of functional groups conjugated with a therapeutic agent. Indeed, any particular arrangement of the therapeutic agent and functional groups is contemplated as an acceptable and functional embodiment. In some embodiments, the functional agents are configured such that a first functional group is linked to the therapeutic agent, and a second functional group is linked to the therapeutic agent. In some embodiments, the functional groups are configured such that the therapeutic agent is linked to a first functional group, and the second functional group is linked to the first functional group. As such, the pro-drug complexes of the present invention contemplate direct and indirect conjugation of the functional groups with the therapeutic agent (e.g., direct: functional group 1—therapeutic agent—functional group 2) (e.g., indirect: therapeutic agent—functional group 1—functional group 2).

The functional groups (e.g., trigger agent, imaging agent, targeting agent) are not limited to a particular manner of conjugation with the therapeutic agent within a pro-drug complex. For example, in some embodiments, functional groups are specifically conjugated to a respective therapeutic agent. In some embodiments, functional groups are covalently conjugated to a respective therapeutic agent. In some embodiments, functional groups are conjugated to a respective therapeutic agent via a linker.

A multiplicity of linkers find use in the present invention (e.g., linkers connecting functional groups with therapeutic agents within pro-drug complexes). In some embodiments, the linker comprises a spacer comprising between 1 and 50 straight or branched carbon chains. In some embodiments, the straight or branched carbon chains are unsubstituted. In some embodiments, the straight or branched carbon chains are substituted with alkyls. In some embodiments, the linker is

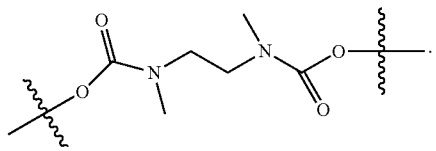 [SMILES: *OC(=O)N(C)CCN(C)C(=O)O*]

In some embodiments, the linker is an aliphatic chain tether (e.g., a polyethylene glycol (PEG) chain (e.g., from 1 PEG unit to, for example, 100 PEG units)).

In some embodiments, the linker is configured such that its decomposition leads to the liberation (e.g., non-reversible liberation) of the therapeutic agent (e.g., at the target site (e.g., site of tumor, CNS, and/or inflammatory site)). The linker may influence multiple characteristics of the pro-drug complex (e.g., therapeutic agent conjugated with at least one functional group) including, but not limited to, properties of the therapeutic agent (e.g., stability, pharmacokinetic, organ distribution, bioavailability, and/or enzyme recognition (e.g., when the therapeutic agent is enzymatically activated)).

In some embodiments, the linker is an elimination linker. For example, in some embodiments, in a pro-drug complex comprising an elimination linker, when the elimination linker is cleaved (e.g., enzymatically and/or chemically), a phenol or an aniline promotes a facile 1,4 or 1,6 elimination, followed by release of a $CO_2$ molecule and the unmasked therapeutic agent (e.g., drug). In some embodiments, a pro-drug complex of the present invention utilizes this configuration and/or strategy to mask one or more hydroxyl groups and/or amino groups of the therapeutic agents. In some embodiments, a linker present within a pro-drug complex of the present invention is fine tuned (e.g., to optimize stability and/or therapeutic agent release from the conjugate). For example, the sizes of the aromatic substituents can be altered (e.g., increased or decreased) and/or alkyl substitutions at the benzylic position may be made to alter (e.g., increase or decrease) degradation of the linker and/or release of the therapeutic agent. In some embodiments, elongated analogs (e.g., double spacers) are used (e.g., to decrease steric hindrance (e.g., for large therapeutic agents)). In some embodiments, a pro-drug complex (e.g., a therapeutic agent conjugated with at least one functional group) of the present invention comprises an enol based linker (e.g., that undergoes an elimination reaction to release the therapeutic agent).

In some embodiments, the linker is a cyclization based linker. A nucleophilic group (e.g., OH or NHR) that becomes available once the cyclization based linker is cleaved attacks the carbonyl of the C(O)X-Therapeutic agent/drug (e.g., thereby leading to release of therapeutic agent-XH) and thereby to quickly release the Drug-XH. In some embodiments, a driving force that permits the reaction to reach completion is the stability of the cyclic product.

In some embodiments, a pro-drug complex (e.g., a therapeutic agent conjugated with at least one functional group) of the present invention comprises a combination of one or more linkers. For example, in some embodiments, a pro-drug complex comprises a combination of two or more elimination linkers. In some embodiments, a pro-drug complex of the present invention comprises two or more cyclization linkers. In some embodiments, a pro-drug complex of the present invention comprises a one or more elimination linkers and one or more cyclization linkers, or a combination of one or more different types of linkers described herein. In some embodiments, a pro-drug complex of the present invention comprises branched self-elimination linkers. In some embodiments, the linkers are used to conjugate a functional group to a therapeutic agent. In some embodiments, the linkers are used to conjugate a functional group to an additional functional group.

In some embodiments, the linker is a self-immolative connector between an ester bond (e.g., that is to be cleaved) and the therapeutic agent (e.g., thereby enhancing drug release). For example, although a mechanism is not necessary to practice the present invention and the present invention is not limited to any particular mechanism of action, in some embodiments, a pro-drug complex of the present invention comprising an ester linkage undergoes esterase catalyzed hydrolysis.

In some embodiments, linkage between a therapeutic agent and a functional group, or between a first functional group and a second functional group, comprises a non-cleavable bond (e.g., an ether or an amide bond (e.g., thereby decreasing unwanted activation of a trigger and/or degradation of a linker and/or release of therapeutic drug).

The present invention is not limited by the type of linker configuration. In some embodiments, the linker is conjugated via a free amino group via an amide linkage (e.g., formed from an active ester (e.g., the N-hydroxysuccinimide ester)). In some embodiments, an ester linkage remains in the conjugate after conjugation. In some embodiments, linkage occurs through a lysine residue. In some embodiments, conjugation occurs through a short-acting, degradable linkage. The present invention is not limited by the type of degradable linkage utilized. Indeed, a variety of linkages are contemplated to be useful in the present invention including, but not limited to, physiologically cleavable linkages including ester, carbonate ester, carbamate, sulfate, phosphate, acyloxyalkyl ether, acetal, and ketal linkages. In some embodiments, a pro-drug complex comprises a cleavable linkage present in the linkage between either the therapeutic agent and a functional group or between two functional groups (e.g., such that when cleaved, no portion of the linkage remains on the prodrug complex). In some embodiments, a pro-drug complex comprises a cleavable linkage present in the linker itself (e.g., such that when cleaved, a small portion of the linkage remains on the pro-drug complex).

In some embodiments, conjugation between a therapeutic agent and a functional group or between functional groups is accomplished through use of a 1,3-dipolar cycloaddition reaction ("click chemistry"). 'Click chemistry' involves, for example, the coupling of two different moieties (e.g., a therapeutic agent and a functional group) (e.g., a first functional group and a second functional group) via a 1,3-dipolar cycloaddition reaction between an alkyne moiety (or equivalent thereof) on the surface of the first moeity and an azide moiety (or equivalent thereof) (or any active end group such as, for example, a primary amine end group, a hydroxyl end group, a carboxylic acid end group, a thiol end group, etc.) on the second moiety. 'Click' chemistry is an attractive coupling method because, for example, it can be performed with a wide variety of solvent conditions including aqueous environments. For example, the stable triazole ring that results from coupling the alkyne with the azide is frequently achieved at quantitative yields and is considered to be biologically inert (see, e.g., Rostovtsev, V. V.; et al., Angewandte Chemie-International Edition 2002, 41, (14), 2596; Wu, P.; et al., Angewandte Chemie-International Edition 2004, 43, (30), 3928-3932; each herein incorporated by reference in their entireties).

In some embodiments, the pro-drug complex comprises a therapeutic agent and one or more functional groups, wherein each of said one or more functional groups is selected from a targeting agent, a trigger agent, and an imaging agent. The arrangement of the therapeutic agent and the one or more functional groups is not limited to a particular configuration. Indeed, in some embodiments, the arrangement of the therapeutic agent and the one or more functional groups is represented by one of the following formulas:

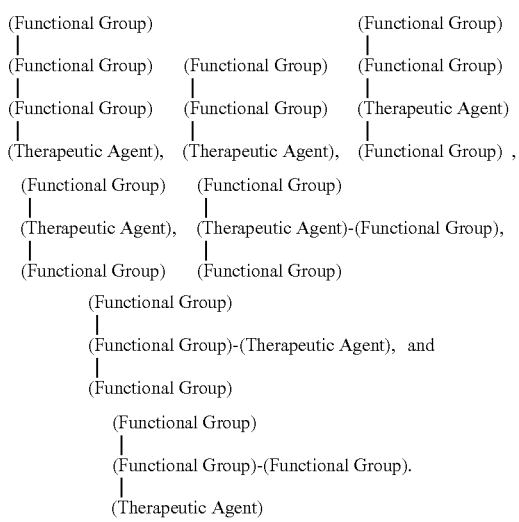

In some embodiments, the therapeutic agent is, for example, a chemotherapeutic agent, an anti-oncogenic agent, an anti-angiogenic agent, a tumor suppressor agent, an anti-microbial agent, an expression construct comprising a nucleic acid encoding a therapeutic protein, etc. In some embodiments, the therapeutic agent is a camptothecin derivative such as, for example, SN-38.

In some embodiments, the trigger agent is configured, for example, to delay release of the therapeutic agent, to constitutively release the therapeutic agent, to release the therapeutic agent under conditions of acidosis, to release the therapeutic agent under conditions of hypoxia, and to release the therapeutic agent in the presence of a brain enzyme (e.g., DT-diaphorase). In some embodiments, the trigger agent is, for example, an ester bond, an amide bond, an ether bond, an indoquinone, a nitro-heterocyle, and a nitroimidazole. In some embodiments, the trigger agent is indolequinone.

In some embodiments, the imaging agent is fluorescein isothiocyanate or 6-TAMARA.

In some embodiments, the targeting agent is configured to target the pro-drug complex to cancer cells. Examples of such targeting agents include, but are not limited to, c(RGDyK), folic acid, CFTR, EGFR, estrogen receptor, FGR2, folate receptor, IL-2 receptor, and VEGFR. In some embodiments, the targeting agent is an antibody that binds to a polypeptide selected from, for example, p53, Muc1, a mutated version of p53 that is present in breast cancer, HER-2, T and Tn haptens in glycoproteins of human breast carcinoma, and MSA breast carcinoma glycoprotein. In some embodiments, the antibody is human carcinoma antigen, TP1 and TP3 antigens from osteocarcinoma cells, Thomsen-Friedenreich (TF) antigen from adenocarcinoma cells, KC-4 antigen from human prostrate adenocarcinoma, human colorectal cancer antigen, CA125 antigen from cystadenocarcinoma, DF3 antigen from human breast carcinoma, and p97 antigen of human melanoma, carcinoma or orosomucoid-related antigen.

In some embodiments, one or more of the attachments between the therapeutic agent and one or more of the functional groups (or the attachment between the functional groups) are accomplished with a linker. In some embodiments the linker has a spacer comprising between 1 and 50 straight or branched (e.g., substituted or unsubstituted) carbon chains. In some embodiments, the linker is

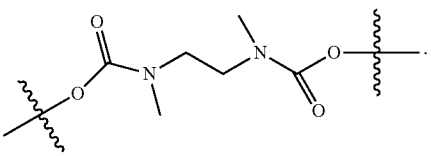 [SMILES: *OC(=O)N(C)CCN(C)C(=O)O*]

In some embodiments, one or more of the attachments between the therapeutic agent and one or more of the functional groups (or the attachment between the functional groups) are accomplished with via a 1,3 dipolar cycloaddition reaction. In some embodiments, one or more of the attachments between the therapeutic agent and one or more of the functional groups (or the attachment between the functional groups) comprises a triazole ring.

In some embodiments, the pro-drug complex is represented by the formula: R1-R2-R3, wherein R1 is SN-38, R2 is indolequinone, and R3 is c(RGDyK). In such embodiments, R1 and R2 and conjugated via a linker represented by

25

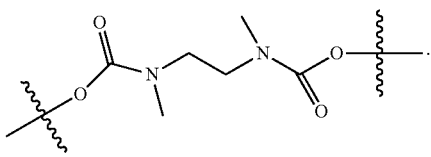 [SMILES: *OC(=O)N(C)CCN(C)C(=O)O*]

In such embodiments, R2 and R3 are conjugated via an attachment comprising a triazole ring (e.g., via a 1,3 cycloaddition reaction).

In some embodiments represented by the formula: R1-R2-R3 (wherein R1 is SN-38, R2 is indolequinone, R3 is c(RGDyK), R1 and R2 and conjugated via a linker represented by

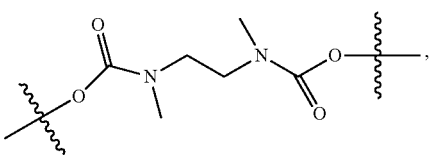 [SMILES: *OC(=O)N(C)CCN(C)C(=O)O*]

and R2 and R3 are conjugated via an attachment comprising a triazole ring, the pro-drug complex is represented by the following structure:

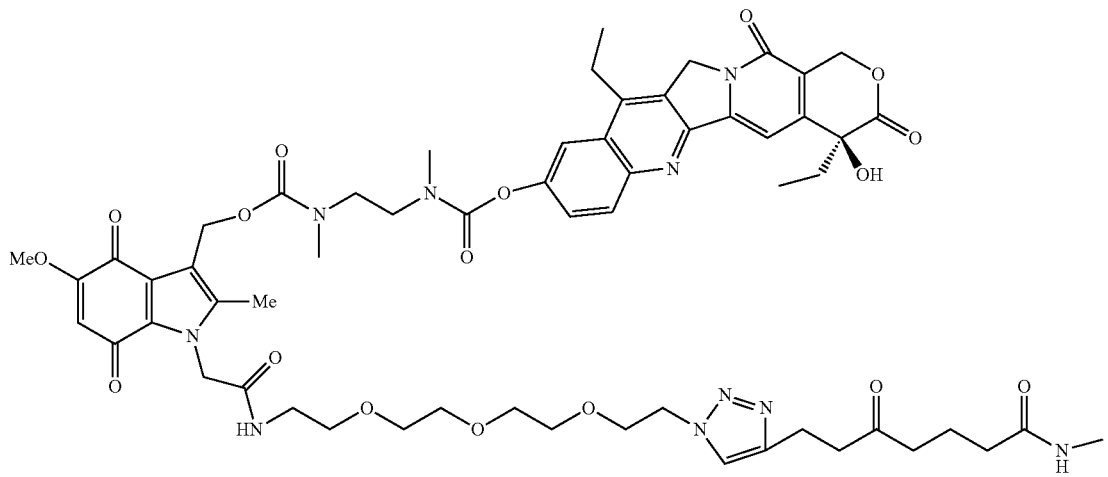

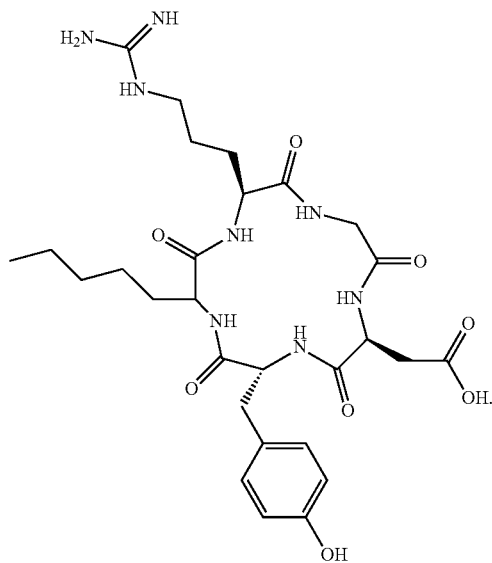

It is contemplated that pro-drug complexes provide therapeutic benefits to patients suffering from cancer. Accordingly, one aspect of the invention relates to a method of treating a subject suffering from cancer. The method comprises administering to a subject in need thereof a therapeutically effective amount of one or more of the pro-drug complexes described herein (e.g., embodiments, the cancer is colon cancer, small-cell lung cancer, non-small cell lung cancer, renal cancer, ovarian cancer, renal cancer, or melanoma.

Additional exemplary cancers include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Ewing's

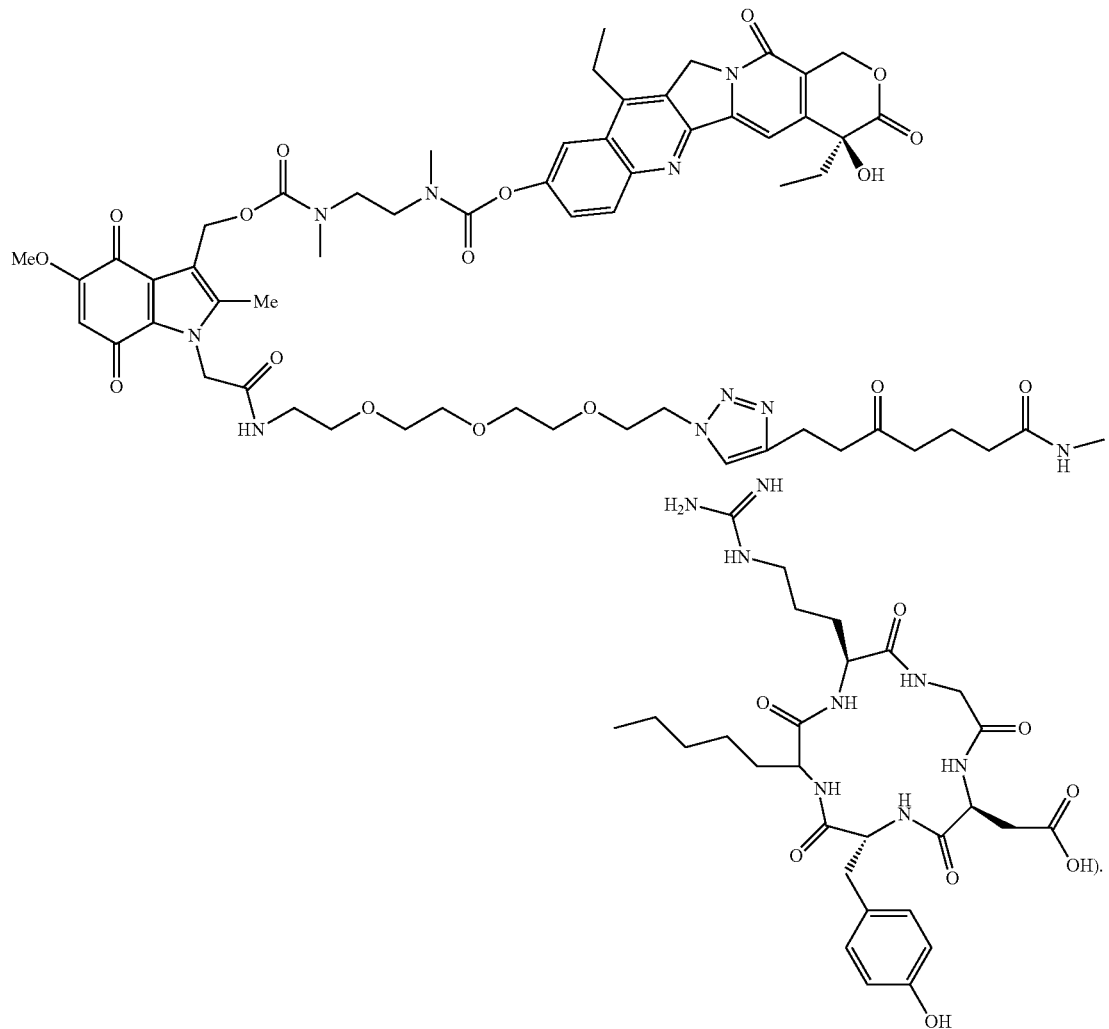

The pro-drug complexes described herein are contemplated to have activity in treating a variety of cancers. For example, the pro-drug complexes described herein are contemplated to have activity in treating a hematological cancer or solid tumor malignancy. In certain embodiments, the cancer is breast cancer, colon cancer, small-cell lung cancer, non-small cell lung cancer, prostate cancer, renal cancer, ovarian cancer, leukemia, melanoma, cancer of the central nervous system tissue, pancreatic cancer, cervical cancer, testicular cancer, bladder cancer, brain cancer, skin cancer, thyroid cancer, Hodgkin's lymphoma, non-Hodgkin's lymphoma, cutaneous T-Cell lymphoma, cutaneous B-Cell lymphoma, or diffuse large B-Cell lymphoma. In certain other embodiments, the cancer is breast cancer, colon cancer, small-cell lung cancer, non-small cell lung cancer, prostate cancer, renal cancer, ovarian cancer, leukemia, melanoma, or cancer of the central nervous system tissue. In certain other tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, epithelial carcinoma, glioma, astrocytoma, medulloblastoma, hemangioblastoma, acoustic neuroma, oligodendroglioma, meningioma, neuroblastoma, and retinoblastoma.

In certain embodiments, the caner is a neuroblastoma, meningioma, hemangiopericytoma, multiple brain metastase, glioblastoma multiforms, glioblastoma, brain stem glioma, poor prognosis malignant brain tumor, malignant glioma, anaplastic astrocytoma, anaplastic oligodendroglioma, neuroendocrine tumor, rectal adeno carcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma, localized melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, *fibrodysplasia ossificans* progressive, hormone refractory prostate cancer, resected high-risk soft tissue sarcoma, unrescectable hepatocellular carcinoma, Waidenstrom's macroglobulinemia, smoldering myeloma, indolent myeloma, fallopian tube cancer, androgen independent prostate cancer, androgen dependent stage 1V non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

The present invention also includes methods involving co-administration of the pro-drug complexes described herein with one or more additional active agents. Indeed, it is a further aspect of this invention to provide methods for enhancing prior art therapies and/or pharmaceutical compositions by co-administering pro-drug complexes of this invention. In co-administration procedures, the agents may be administered concurrently or sequentially. In some embodiments, the pro-drug complexes described herein are administered prior to the other active agent(s). The agent or agents to be co-administered depends on the type of condition being treated. For example, when the condition being treated is cancer, the additional agent can be a chemotherapeutic agent or radiation. The additional agents to be co-administered, such as anticancer agents, can be any of the well-known agents in the art, including, but not limited to, those that are currently in clinical use. The determination of appropriate type and dosage of radiation treatment is also within the skill in the art or can be determined with relative ease.

Another aspect of the invention provides pharmaceutical compositions which comprise a therapeutically-effective amount of one or more of the pro-drug complexes described herein, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations. (See e.g., Martin, Remington's Pharmaceutical Sciences, 15th Ed., Mack Publ. Co., Easton, Pa. [1975]; herein incorporated by reference in its entirety).

The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19; herein incorporated by reference in its entirety)

The pharmaceutically acceptable salts of the pro-drug complexes include the conventional nontoxic salts or quaternary ammonium salts of the pro-drug complexes, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the pro-drug complexes of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of pro-drug complexes of the present invention.

These salts can likewise be prepared in situ in the administration vehicle or the dosage form manufacturing process, or by separately reacting the purified pro-drug complex in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (See, for example, Berge et al. (1977) "Pharmaceutical Salts", J. Pharm. Sci. 66:1-19; herein incorporated by reference in its entirety).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a pro-drug complex of the present invention.

Methods of preparing these formulations or compositions include the step of bringing into association a pro-drug complex of the present invention with the carrier and, optionally, one or more accessory ingredients. In general, the formulations are prepared by uniformly and intimately bringing into association a pro-drug complex of the present invention with liquid carriers, or finely divided solid carriers, or both, and then, if necessary, shaping the product. In certain embodiments, the invention provides for the use of a pro-drug complex described herein in the manufacture of a medicament for the treatment of a disease or disorder described herein.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A pro-drug complex of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active pro-drug complexes, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active pro-drug complex.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc.

administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These pro-drug complexes may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular pro-drug complex of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the pro-drug complexes of this invention for a patient, when used for the indicated analgesic effects, will range from about 0.0001 to about 100 mg per kilogram of body weight per day.

If desired, the effective daily dose of the active pro-drug complex may be administered as two, three, four, five, six or more sub-doses administered separately at appropriate intervals throughout the day, optionally, in unit dosage forms. Preferred dosing is one administration per day.

While it is possible for a pro-drug complex of the present invention to be administered alone, it is preferable to administer the pro-drug complex as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or non-aqueous diluents, syrups, granulates or powders. In addition to an agent of the present invention, the pharmaceutical compositions can also contain other pharmaceutically active compounds or a plurality of compounds of the invention.

EXAMPLES

The invention now being generally described, will be more readily understood by reference to the following examples, which are included merely for purposes of illustration of certain aspects and embodiments of the present invention, and are not intended to limit the invention.

Example 1

Synthesis of the c(RGDyK) Targeted SN38 Prodrug

1. Synthesis of Non-Targeted Pro-Drug.

As shown in FIG. 1, commercially available 5-methoxy-2-methylindole was first treated with Vilsmeier reagents to give 3-formyl compound 2 with excellent yield. Alkylation of position 1 was then carried out with sodium hydride and ethyl bromo-acetate. Nitration at the desired 4-position could only be achieved at a low reaction concentration and with a large excess of nitric acid. However, a 6-nitro isomer was presented at a low ratio (about 15%). The mixture had poor solubility in organic solvents, making it impossible to purify through chromatography. The mixture was reduced with Sn/HCl to give a mixture of 4- and 6-amine products. The desired 4-amino compound 5 was then purified with chromatography. Fremy's salt was then used to covert the aromatic ring to a quinone structure with quantitative yield. The crucial step is the reduction of the 3-carboxaldehyde to a hydroxyl group. There are several other sites which can also be reduced in the structure, especially the ethyl ester. Selective reduction of the aldehyde rather than the ester could only be achieved by using 5 equivalents of NaBH4 at 0° C. over 8 minutes. An elevated temperature and a prolonged reaction time would decrease the yield drastically. The yield of the reduction reaction was around 60%. After the hydrolysis of the ester with 1 equivalent of LiOH, the compound 8 was then coupled with an azido amine tether to give indolequinone linker 9 with a clickable tether which can be reacted with reactants with an alkyne functional group through 1,3-Huisgen cyclic addition.

Figure 2:
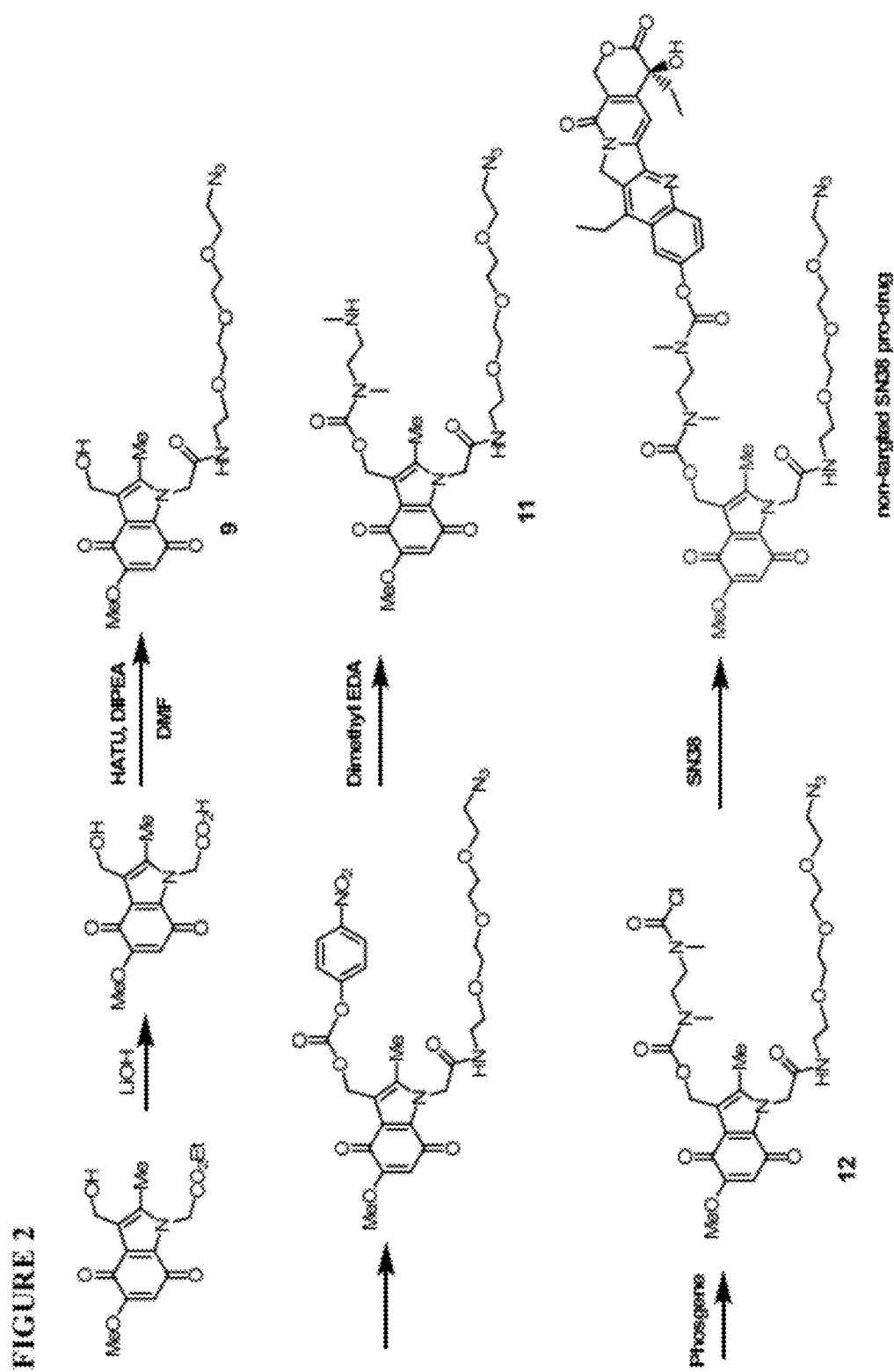
FIG. 2 shows a synthesis scheme for a non-targeted SN-38 pro-drug.
Figure 3:
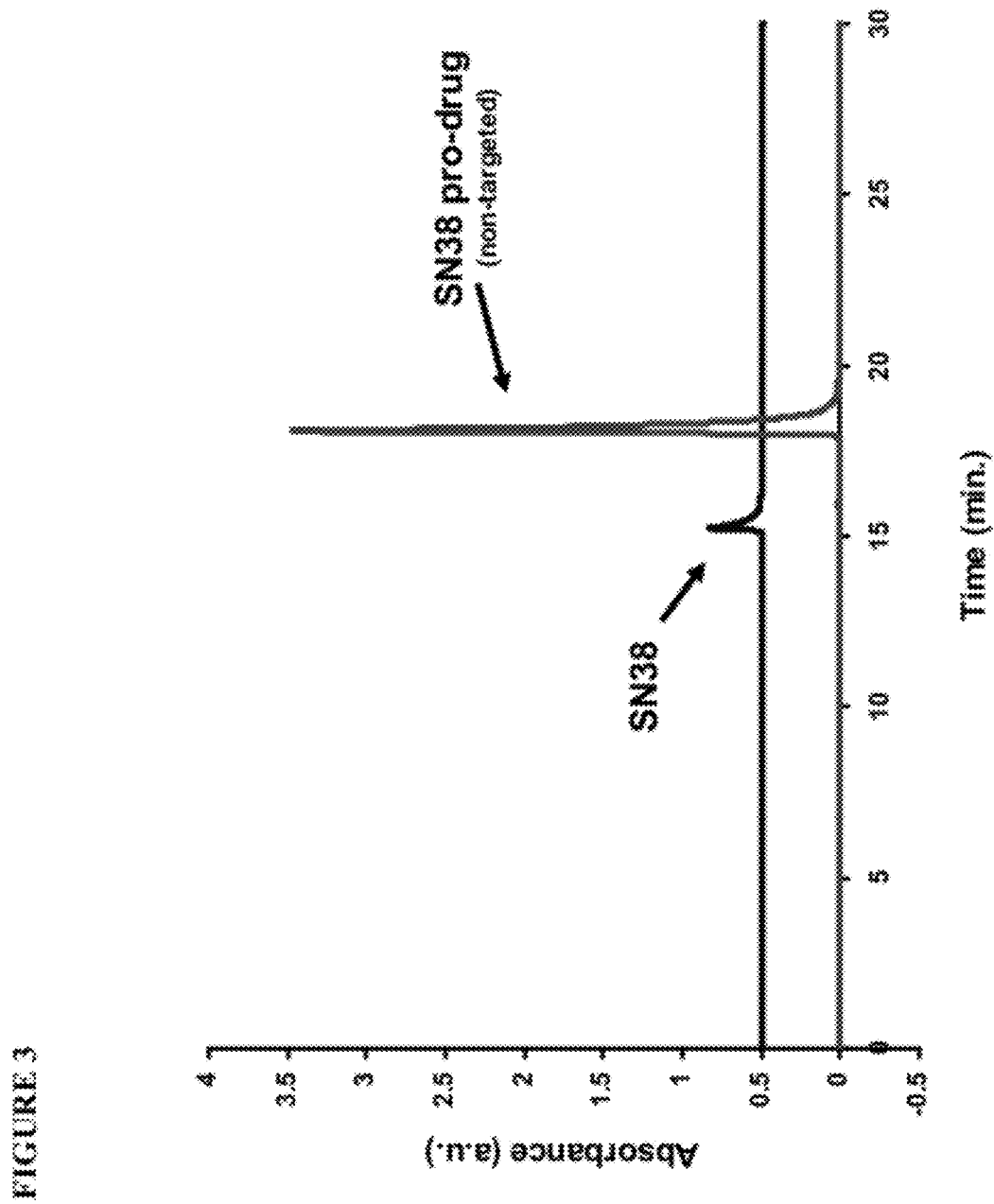
FIG. 3 shows a HPLC profile for non-targeted SN-38 pro-drug and free SN-38.

FIG. 2 shows the synthesis schmem for non-targeted SN38 pro-drug. In order to reduce the steric interference between the drug and the linker and thus enhance the release rate, an elongated spacer N,N'-methylethylenediamine was incorporated between the indolequinone linker moiety and the drug. In the mean time, carbamate bonds between the indolequinone and naloxone make the structure stable in buffer conditions. To achieve this, the activated 4-nitrophenyl carbonate of compounds 9 was condensed with an excess of N,N'-methylethylene diamine to give the compounds 10. Only a 3 equivalent of diamine was used in the reactions without a significant amount of dimerization. The secondary amine at compound 10 was then converted to a carbomyl chloride, which was subsequently reacted with SN38 in the presence TEA and DMAP to form the SN38 pro-drug. All compounds were characterized with NMR and MS spectra. The HPLC profile for the non-targeted pro-drug is shown in FIG. 3.

2. Synthesis of the c(RGDyK) Targeted Pro-Drug.

Figure 4:
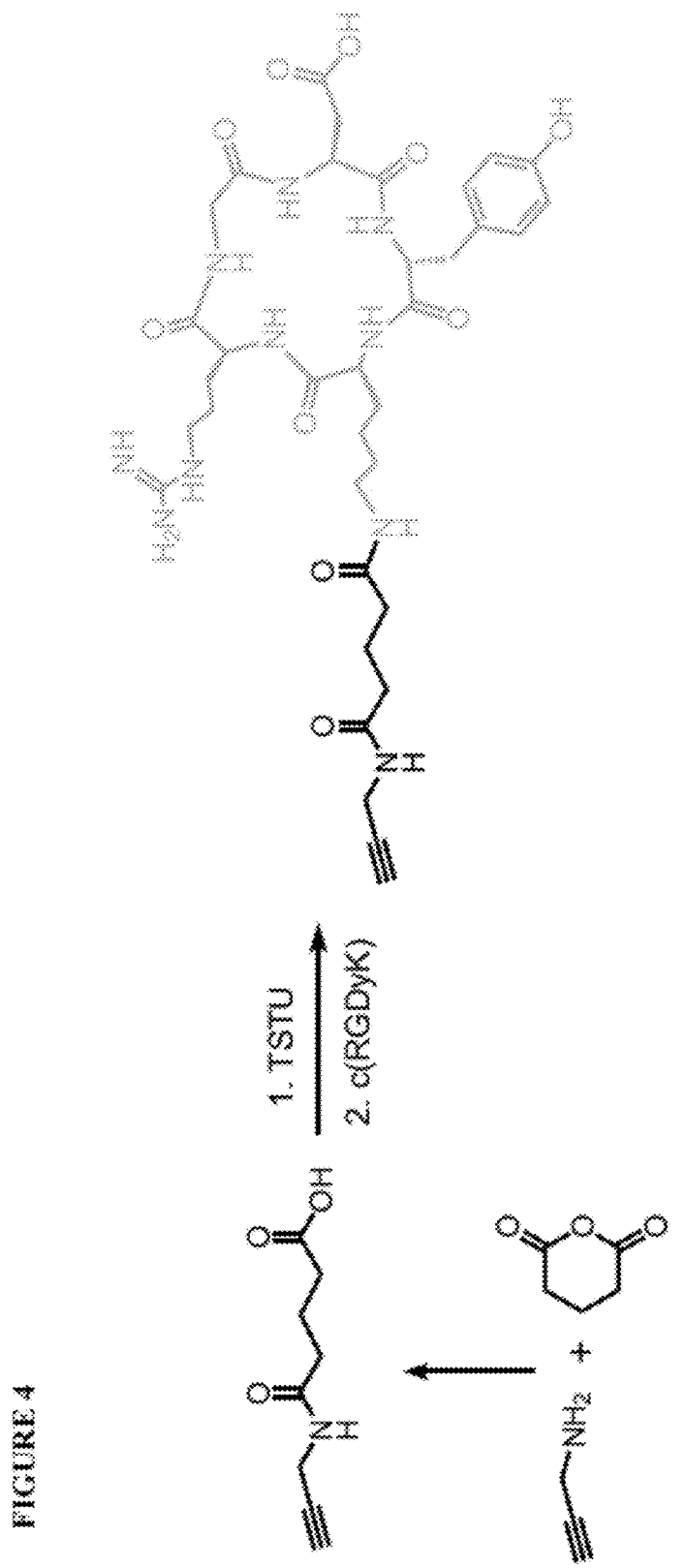
FIG. 4 shows a modification scheme of c(RGDyK).
Figure 5:
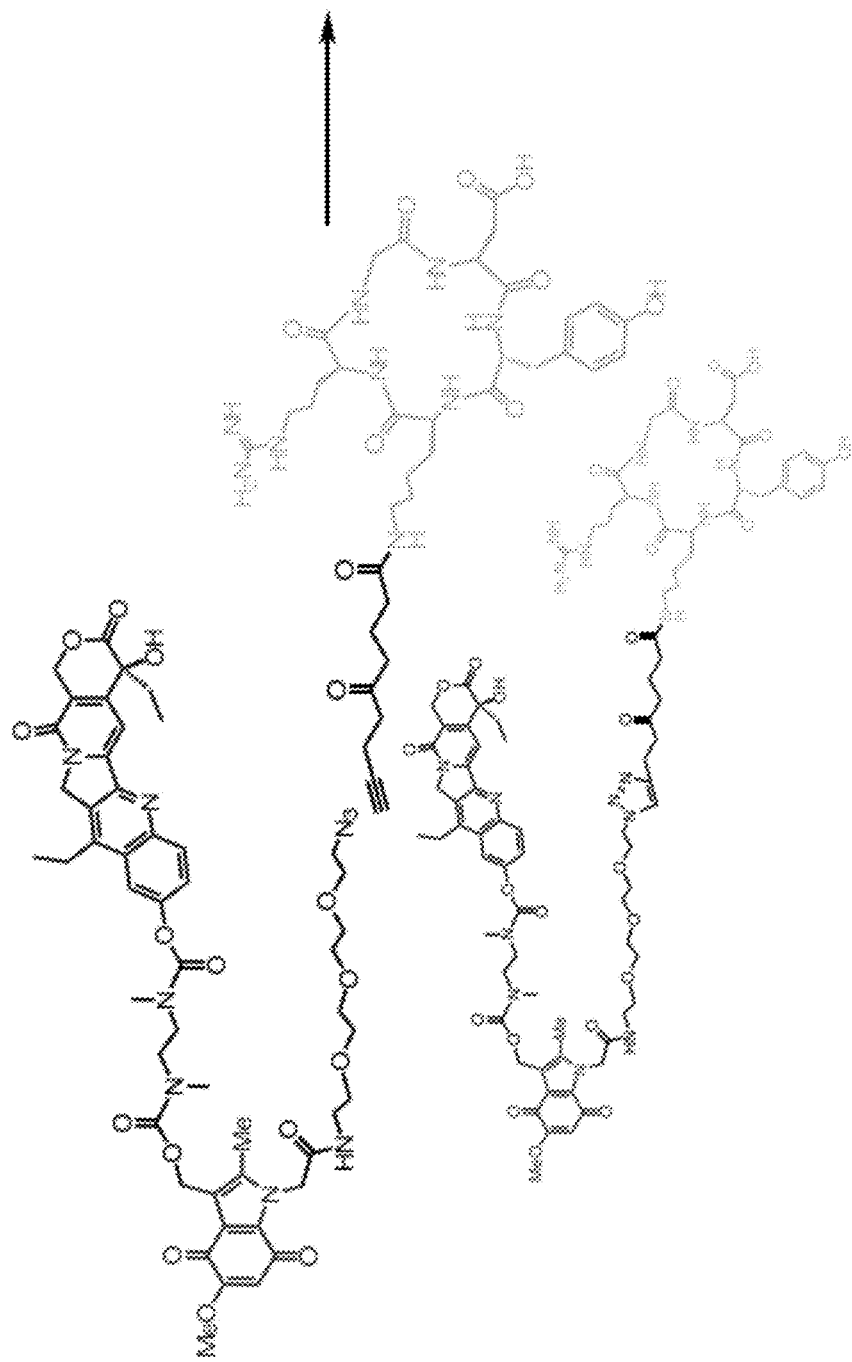
FIG. 5 shows a synthesis scheme for a SN-38 pro-drug complex.

As shown in FIG. 4, the cyclic RGDyK was first modified to a clickable (for click reaction) c(RGDyK). Prep-HPLC was used to purify the product. Then the non-targeted prodrug was reacted with the modified c(RGDyK) by click chemistry to give the targeted pro-drug. (FIG. 5). The HPLC profile for

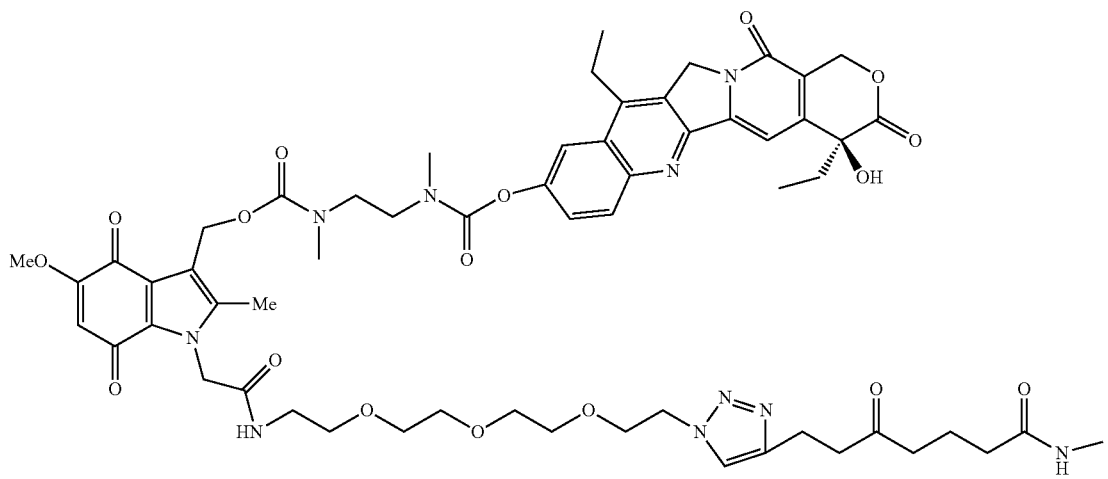

Figure 6:
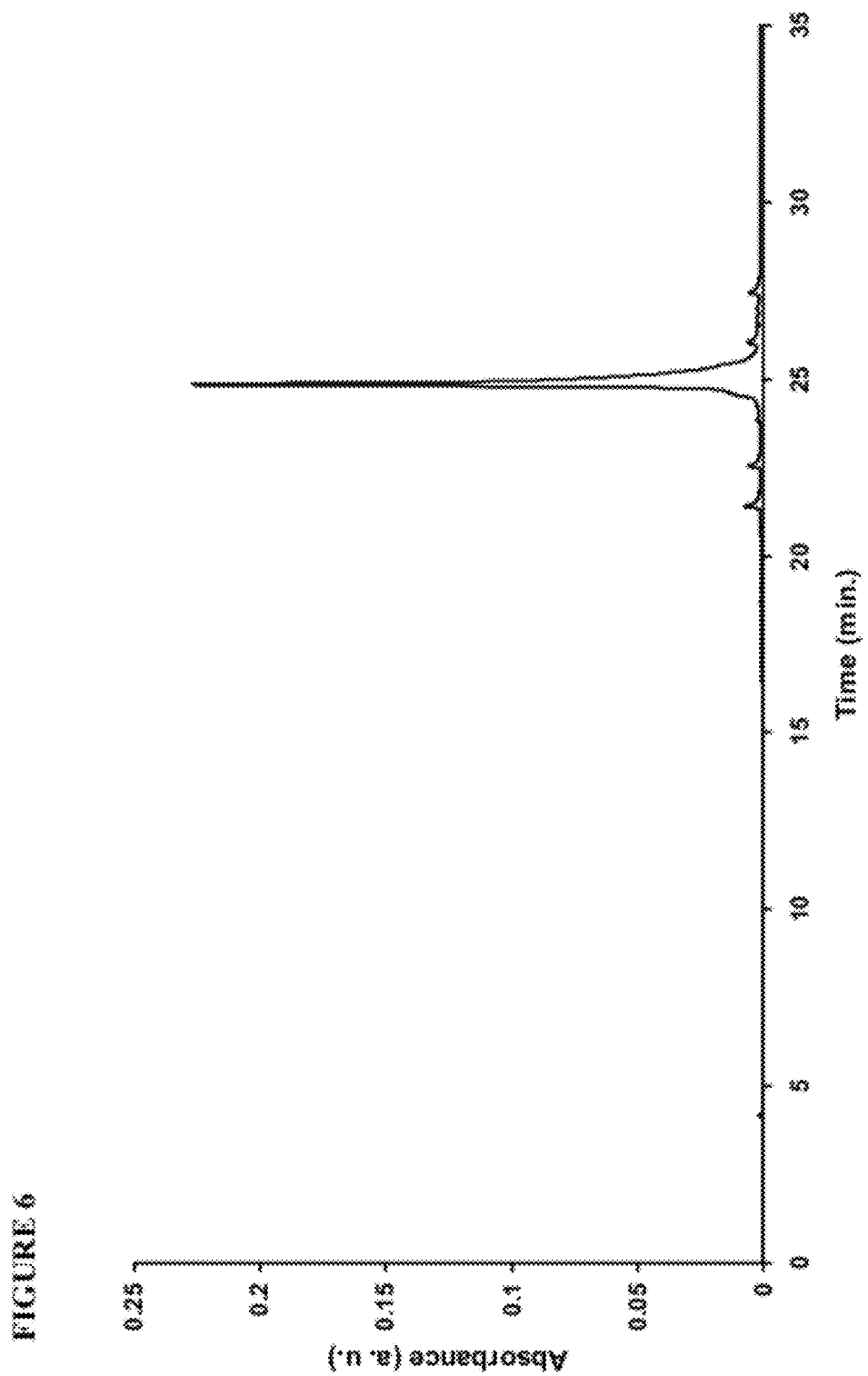
FIG. 6 shows a HPLC profile for the SN-38 pro-drug complex.
Figure 7:
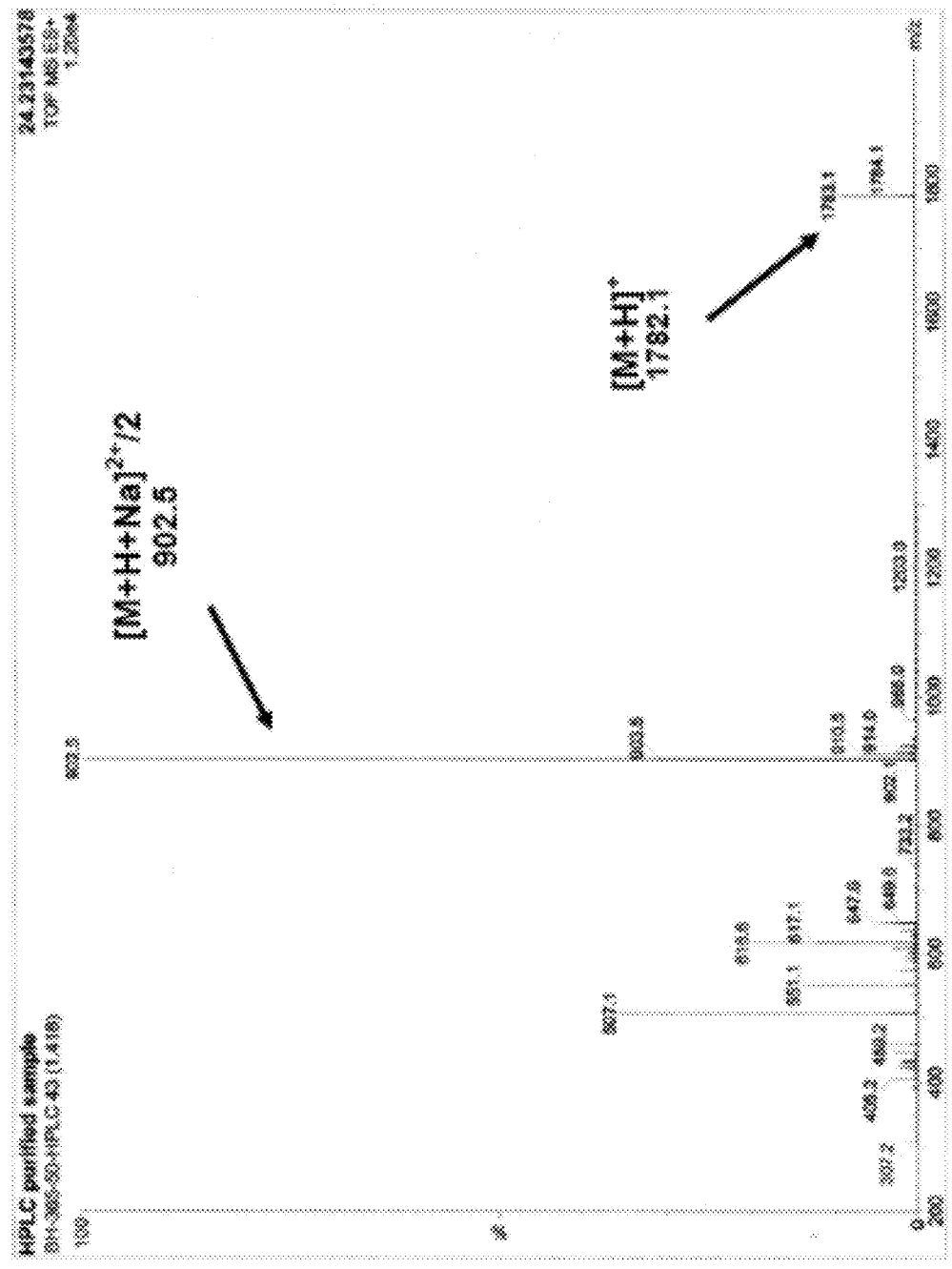
FIG. 7 shows the mass spectrum for a SN-38 pro-drug complex.
Figure 8:
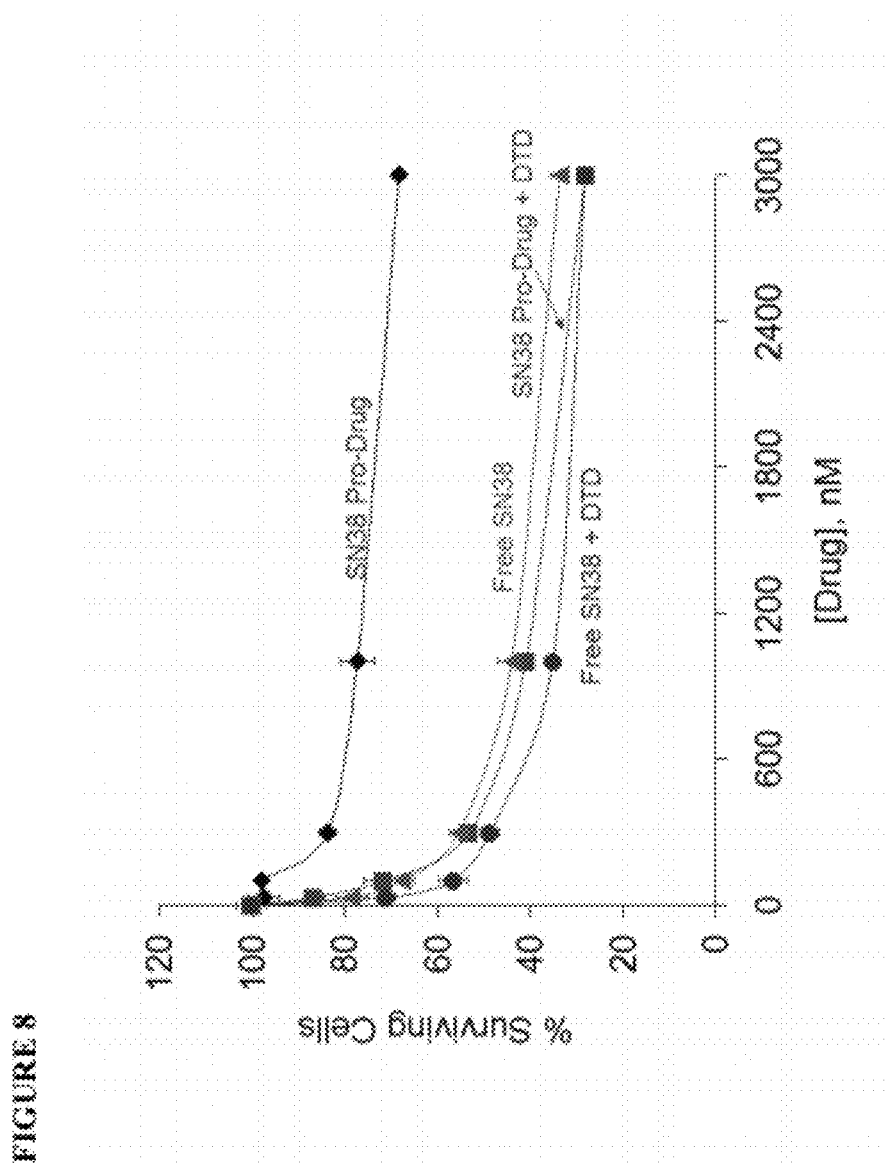
FIG. 8 shows that redox mediated activation of SN-38 pro-drug complex leads to KB cell cytotoxicity.
Figure 9:
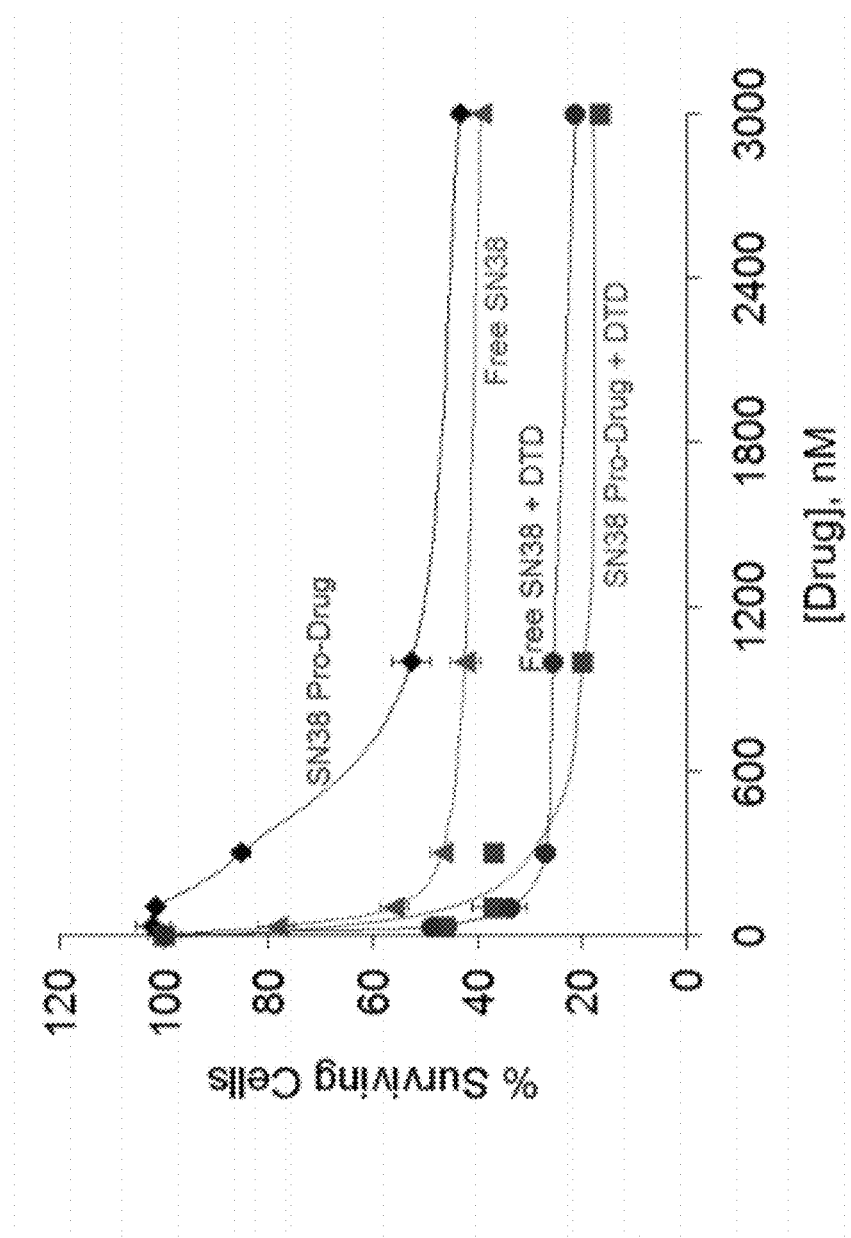
FIG. 9 shows that redox-mediated activation of SN-38 pro-drug complex leads to SKBR3 cell cytotoxicity.

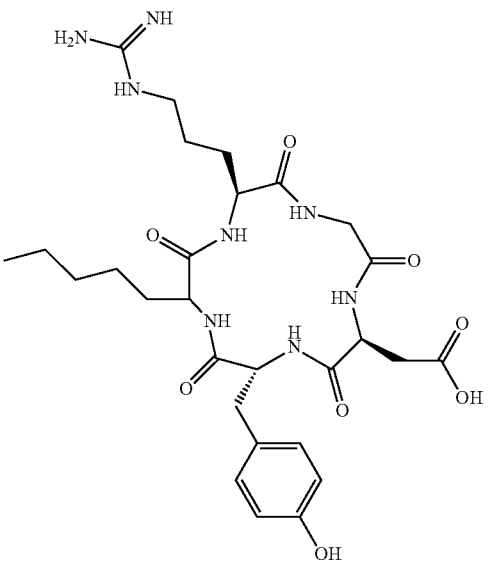
is shown in FIG. 6, and the mass spectrum in FIG. 7.
Example 2
Solubility of SN-38 Prodrug
The solubility of SN-38 pro-drug complex
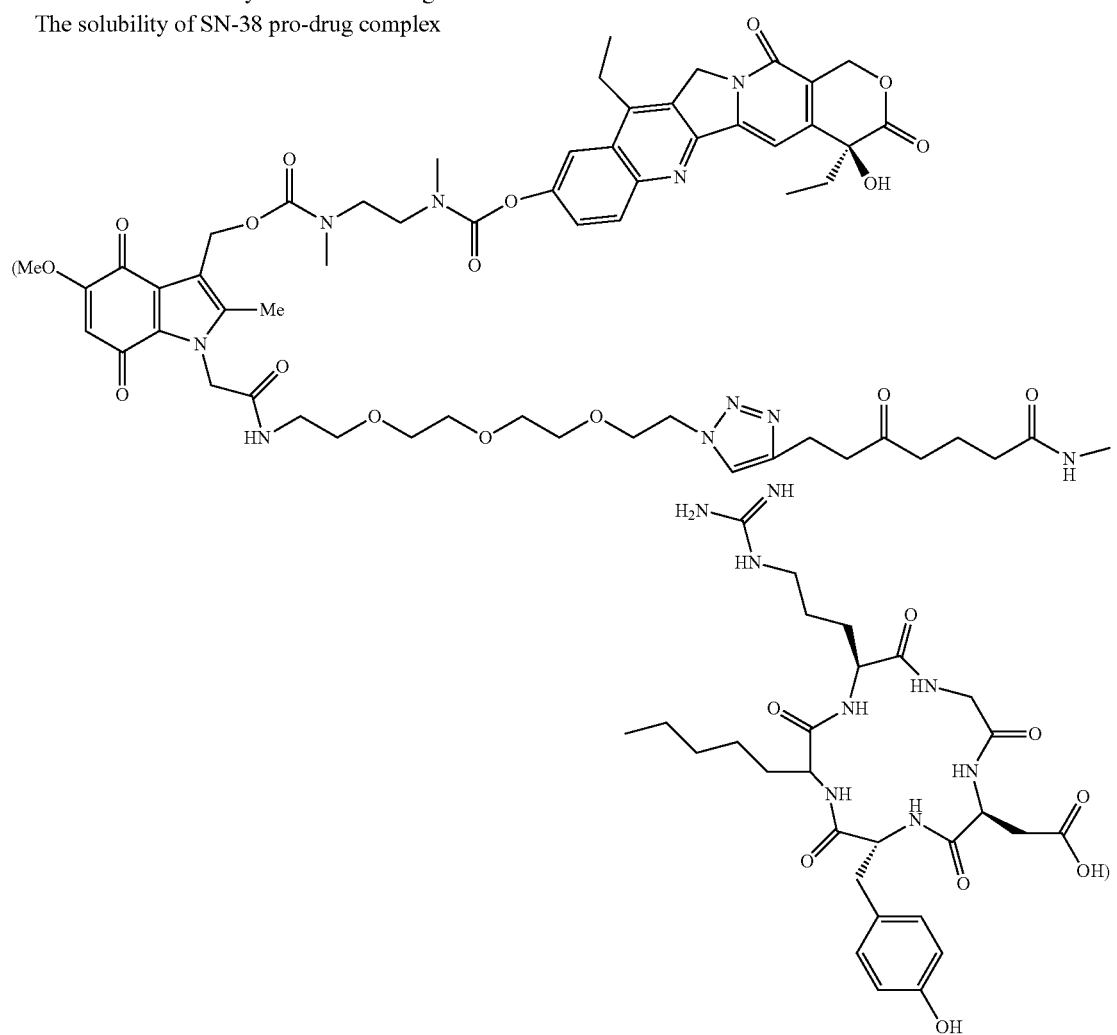

in comparison with SN-38 was investigated. The solubility of SN38 pro-drug complex was shown to be >=50 times compared with SN38. In addition, the SN-38 pro-drug complex was shown to have a solubility of 100 micro gram per milliliter of water versus about 2 micro gram per milliliter for SN38.

Example 3

In Vitro Studies Examining the Cytotoxicity of the SN-38 Prodrug Versus Free SN-38

The redox-coupled release of free SN38 from the SN-38 pro-drug complex using the enzyme DT-Diaphorase (DTD) was investigated. DTD is a cytosolic oxidoreductase which catalyzes the two-electron reduction of quinones using NADH or NADPH as electron donors (see, e.g., Phillips et al, Biochemical Pharmacology 68: 2107-2116 (2004); herein incorporated by reference in its entirety). As the DTD-induced reduction of quinones is known to take place even under normoxic conditions, the enzyme is used as a positive control for testing the release of drugs from quinone-linked drugs. Synthesized SN-38 pro-drug complex was incubated with recombinant human DTD (Sigma) added into the cell growth medium in the presence of different concentration of the SN-38 pro-drug complex. The effect of the drug on cell growth was determined in two different human cell lines, the cervical carcinoma cell line KB, and the breast cancer cell line SKBR3. As shown in FIG. 2 and FIG. 3, in the absence of DTD, in both the cell types, the prodrug was essentially non-cytotoxic to up to 300 nM concentration of the prodrug, whereas there was ~50-70% decrease in cell growth in presence of DTD.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et at, 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in

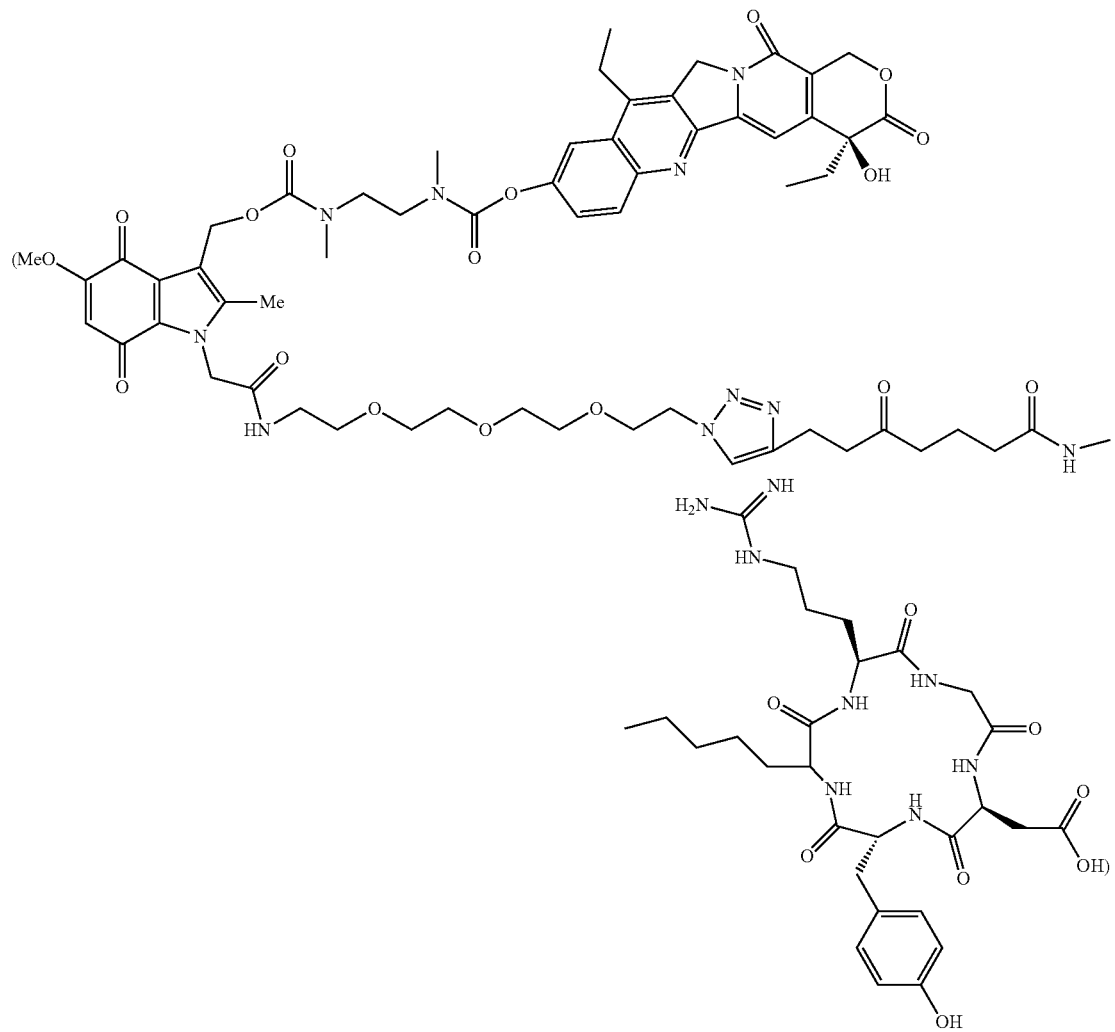

immunology" (J. E. Coligan et al., eds., 1991), each of which is herein incorporated by reference in its entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:
1. A composition comprising a pro-drug complex, wherein said pro-drug complex is represented by the following structure
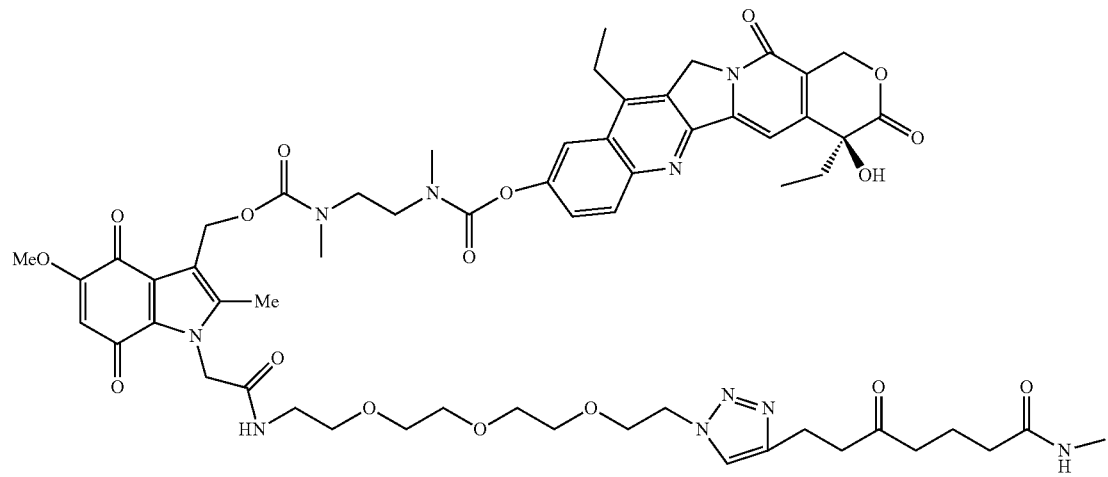
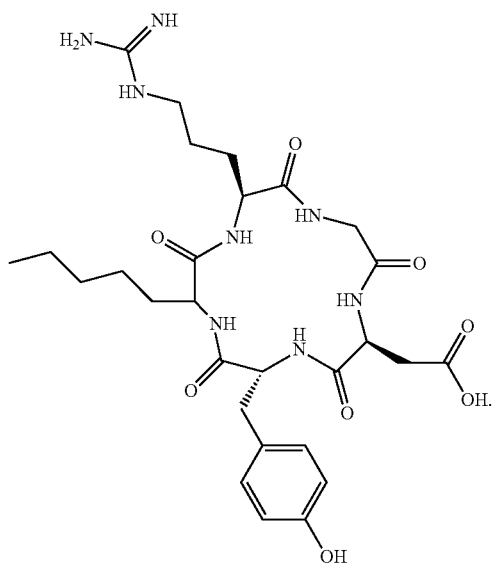

2. A method of treating cancer cells comprising exposing said cancer cells to at least one composition comprising a pro-drug complex, wherein said pro-drug complex is represented by the following structure
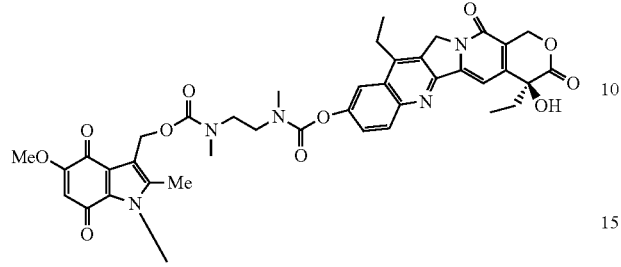
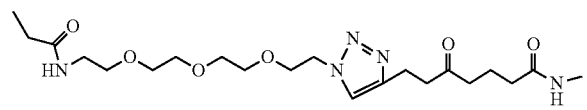
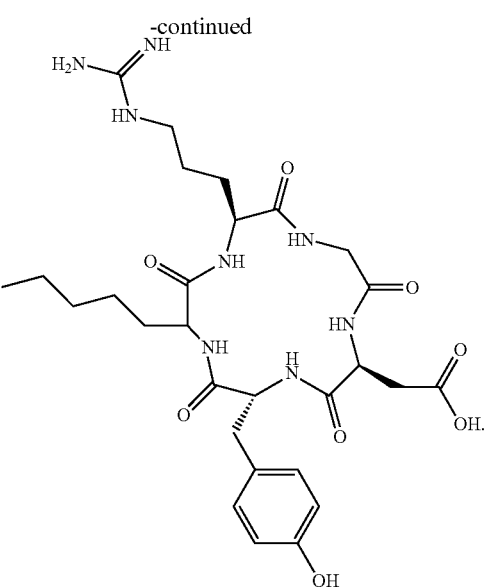
wherein said cancer cells are selected from the group consisting of in vivo, in vitro, and ex vivo.
* * * * *

UNITED STATES PATENT AND TRADEMARK OFFICE
CERTIFICATE OF CORRECTION

PATENT NO. : 8,853,151 B2
APPLICATION NO. : 13/378178
DATED : October 7, 2014
INVENTOR(S) : James R. Baker, Jr. et al.

Page 1 of 1

It is certified that error appears in the above-identified patent and that said Letters Patent is hereby corrected as shown below:

On the title page item (73), please delete

"(73) Assignee: The Regents of the University of Michigan, Ann Harbor, MI (US)"

and replace with:

--(73) Assignee: The Regents of the University of Michigan, Ann Arbor, MI (US)--

Signed and Sealed this
Thirteenth Day of January, 2015

Michelle K. Lee
*Deputy Director of the United States Patent and Trademark Office*